(12) United States Patent
Zheng

(10) Patent No.: US 9,425,408 B2
(45) Date of Patent: Aug. 23, 2016

(54) ORGANIC LIGHT EMITTING HOST MATERIALS

(71) Applicant: NITTO DENKO CORPORATION, Osaka (JP)

(72) Inventor: Shijun Zheng, San Diego, CA (US)

(73) Assignee: NITTO DENKO CORPORATION, Osaka (JP)

( * ) Notice: Subject to any disclaimer, the term of this patent is extended or adjusted under 35 U.S.C. 154(b) by 364 days.

(21) Appl. No.: 14/222,441

(22) Filed: Mar. 21, 2014

(65) Prior Publication Data

US 2014/0284581 A1   Sep. 25, 2014

Related U.S. Application Data

(60) Provisional application No. 61/804,553, filed on Mar. 22, 2013.

(51) Int. Cl.
*H01L 51/50* (2006.01)
*H01L 51/00* (2006.01)
*C07D 405/14* (2006.01)
*C07D 413/14* (2006.01)

(52) U.S. Cl.
CPC .......... *H01L 51/0061* (2013.01); *C07D 405/14* (2013.01); *C07D 413/14* (2013.01); *H01L 51/0071* (2013.01); *H01L 51/0072* (2013.01); *H01L 51/0073* (2013.01); *H01L 51/0037* (2013.01); *H01L 51/0085* (2013.01); *H01L 51/5016* (2013.01); *H01L 2251/308* (2013.01)

(58) Field of Classification Search
None
See application file for complete search history.

(56) References Cited

U.S. PATENT DOCUMENTS

| | | |
|---|---|---|
| 2011/0062386 A1 | 3/2011 | Zheng et al. |
| 2011/0140093 A1 | 6/2011 | Zheng et al. |

FOREIGN PATENT DOCUMENTS

| | | | |
|---|---|---|---|
| JP | 2009155300 | 7/2009 | |
| JP | 2009158848 | 7/2009 | |
| JP | 2010-238880 | * 10/2010 | .............. H01L 51/50 |
| JP | 2010267847 | 11/2010 | |
| WO | WO2010036027 | 4/2010 | |
| WO | WO2011037429 | 3/2011 | |

OTHER PUBLICATIONS

Hu et al., Synthesis of a novel intermediate of organic electrophosphorescent material based on benzimidazole, Huaxue Shiji, 33(2):127-128, 137, (2011).

* cited by examiner

*Primary Examiner* — Gregory Clark
(74) *Attorney, Agent, or Firm* — K&L Gates LLP; Brent A. Johnson; Louis C. Cullman

(57) ABSTRACT

Disclosed herein are compounds represented by formula:

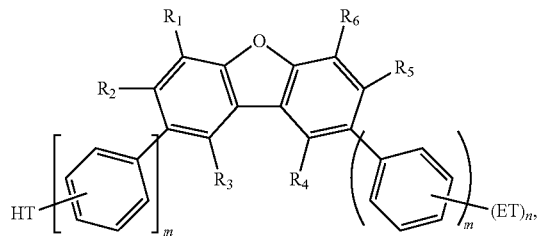

where HT, ET, and $R_1$-$R_6$ are described herein. Compositions of said compounds along with organic light-emitting diode (OLED) devices related thereto are also disclosed.

10 Claims, 1 Drawing Sheet

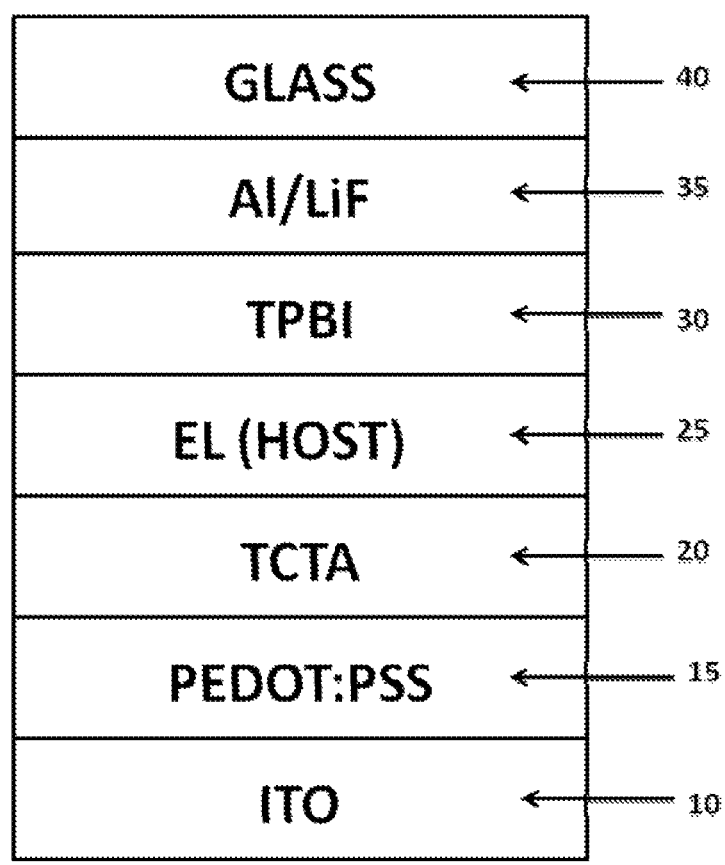

ORGANIC LIGHT EMITTING HOST MATERIALS

FIELD

The present disclosure generally relates to the field of organic chemistry and organic light emitting diodes (OLED). More particularly, the present disclosure pertains to a host material for use in OLED devices.

BACKGROUND

OLED is a flat light emitting technology which utilizes organic thin films placed between two conductors in order to create light. When an electrical current is applied between the two conductors a bright light is emitted. OLED technology has many implementations, including displays, such as televisions, and has been utilized in solid state lighting (SSL) applications. A primary benefit of OLED technology as compared to previous technologies is that OLED technology is more efficient, requiring less electrical consumption, and also allows for space saving because OLED devices can be made very thin.

It is generally considered that a white OLED device, in order to qualify as SSL, needs to achieve greater than 100 lm with color rendering index (CRI) greater than 70 and operating time greater than 10,000 hours at 1000 cd/cm$^2$. To accomplish this, there needs to be a host material capable of supplying such results. Most host materials in existence have problems with low stability, high charge injection barrier, and imbalanced charge injection and mobilities. All of these problems lead to a high turn-on voltage and short device lifetime. In order to achieve high efficiency, low turn-on voltage, and long device lifetime, it may be helpful to create stable, high mobility, bipolar host materials. Achieving these criteria will allow for the realization of the full commercial potential of organic light-emitting devices.

SUMMARY

Some embodiments include a compound represented by the following formula:

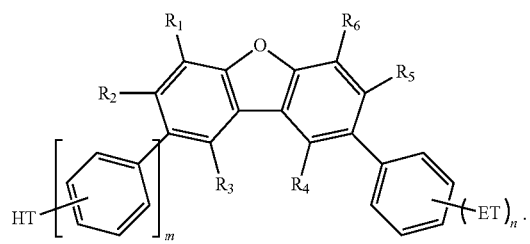

In this host compound formula, where $R_1$, $R_2$, $R_3$, $R_4$, $R_5$ and $R_6$ are independently H, $C_1$-$C_3$ alkyl, or $C_{1-3}$ perfluoroalkyl; HT is optionally substituted carbazoyl, optionally substituted phenylnaphthylamine, or optionally substituted diphenylamine, where each m is independently 0, 1, or 2; and ET is selected from optionally substituted benzimidazol-2-yl, optionally substituted benzothiazol-2-yl, optionally substituted benzoxazol-2-yl, optionally substituted 3,3'-bipyridin-5-yl, optionally substituted quinolin-8-yl, optionally substituted quinolin-5-yl, and optionally substituted quinoxalin-5-yl, where n is 1 or 2.

Another embodiment includes organic light-emitting devices which include a light-emitting layer, said light-emitting layer including a compound described herein.

These and other embodiments are described in greater detail below.

BRIEF DESCRIPTION OF THE DRAWING

FIG. 1 is a schematic diagram of some embodiments of devices described herein.

DETAILED DESCRIPTION

As used herein, unless otherwise indicated, when a chemical structural feature is referred to as being "optionally substituted" it is meant that the feature may have no substitutents (i.e. be unsubstituted) or may have one or more substituents. The term "substituent" has the ordinary meaning known to one of ordinary skill in the art. A substituted group is derived from the unsubstituted parent structure wherein one or more hydrogen atoms on the parent structure have been independently replaced by one or more substituent groups. A substituted group may have one or more substituent groups on the parent group structure. The substituent groups are independently selected from optionally substituted alkyl, —O-alkyl (e.g. —OCH$_3$, —OC$_2$H5, —OC$_3$H$_7$, —OC$_4$H$_9$, etc.), —S-alkyl (e.g. —SCH$_3$, —SC$_2$H$_5$, —SC$_3$H$_7$, —SC$_4$H$_9$, etc.), —NR'R", —OH, —SH, —CN, —NO$_2$, or a halogen, wherein R' and R" are independently H or optionally substituted alkyl. Wherever a substituent is described as "optionally substituted," that substituent can be substituted with the above substituents.

As used herein, the term "benzimidazol-2-yl" refers to the ring system:

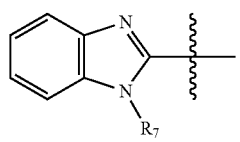

where $R_7$ is selected from the group H, $C_{1-3}$ alkyl, optionally substituted aryl, including, but not limited to phenyl and naphtha.

As used herein, the term "benzoxazol-2-yl" refers to the ring system:

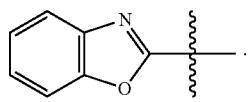 [SMILES: *c1nc2ccccc2o1]

As used herein, the term "benzothiazol-2-yl" refers to the ring system:

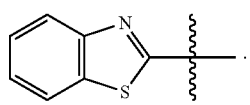 [SMILES: *c1nc2ccccc2s1]

As used herein, the term "3,3'-bipyridin-5-yl" refers to the ring system:

As used herein, the term "quinolin-8-yl" refers to the ring system:

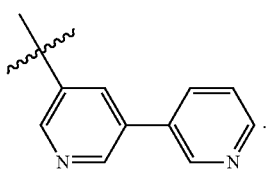 [SMILES: *c1cncc(-c2cccnc2)c1]

As used herein, the term "quinolin-5-yl" refers to the ring system:

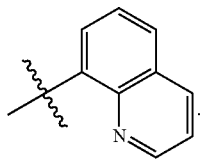 [SMILES: *c1cccc2cccnc12]

As used herein, the term "quinoxalin-5-yl" refers to the ring system:

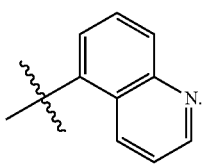 [SMILES: *c1cccc2ncccc12]

As used herein, the term "carbazolyl" refers to the ring system:

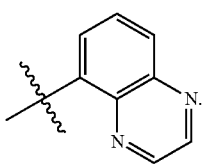 [SMILES: *c1cccc2nccnc12]

which includes, but is not limited to

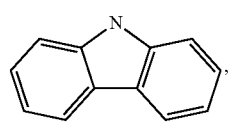 [SMILES: c1ccc2c(c1)[nH]c1ccccc12]

As used herein, the term "diphenylamine" refers to the ring system:

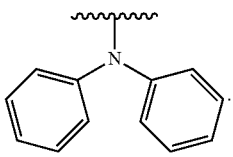 [SMILES: *N(c1ccccc1)c1ccccc1]

As used herein, the term "phenylnaphthylamine" refers to the ring system:

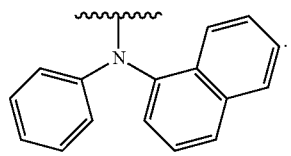 [SMILES: *N(c1ccccc1)c1cccc2ccccc12]

As used herein, the term "1,3 interphenylene" refers to the ring system:

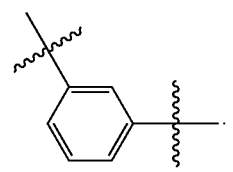 [SMILES: *c1cccc(*)c1]

As used herein, the term "1,4 interphenylene" refers to the ring system:

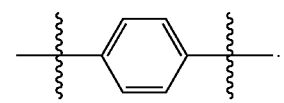

As used herein, the term "perfluoroalkyl" refers to fluoroalkyl with a formula $C_nF_{2n+1}$ for a linear or branched structure, e.g., $CF_3$, $C_2F_5$, $C_3F_7$, $C_4F_9$, $C_5F_{11}$, $C_6F_{13}$, etc., or $C_nF_{2n}$ for a cyclic structure, e.g., cyclic $C_3F_6$, cyclic $C_4F_8$, cyclic $C_5F_{10}$, cyclic $C_6F_{12}$, etc. In other words, every hydrogen atom in alkyl is replaced by fluorine. For example, while not intending to be limiting, $C_{1-3}$ perfluoroalkyl refers to $CF_3$, $C_2F_5$, and $C_3F_7$ isomers.

The term "work function" has the ordinary meaning known to one of ordinary skill in the art. In some embodiments, the "work function" of a metal refers to a measure of the minimum energy required to extract an electron from the surface of the metal.

The term "high work function metal" has the ordinary meaning known to one of ordinary skill in the art. In some embodiments, a "high work function metal" includes a metal or alloy that easily injects holes and typically has a work function greater than or equal to 4.5.

The term "low work function metal" has the ordinary meaning known to one of ordinary skill in the art. In some embodiments, a "low work function metal" includes a metal or alloy that easily loses electrons and typically has a work function less than 4.3.

The expression "white light-emitting" has the ordinary meaning known to one of ordinary skill in the art. In some embodiments, a material is white light-emitting if it emits white light. In some embodiments, white light is light having the approximate CIE color coordinates (X=⅓, Y=⅓). The CIE color coordinates state may be defined as the achromatic point. The X and Y color coordinates may be weights applied to the CIE primaries to match a color. A more detailed description of these terms may be found in CIE 1971, International Commission on Illumination, Colorimetry: Official Recommendations of the International Commission on Illumination, Publication CIE No. 15 (E-1.3.1) 1971, Bureau Central de la CIE, Paris, 1971 and in F. W. Billmeyer, Jr., M. Saltzman, *Principles of Color Technology*, $2^{nd}$ edition, John Wiley & Sons, Inc., New York, 1981 both of which are hereby incorporated by reference in their entireties. The color rendering index (CRI) refers to the ability to render various colors and has values ranging from 0 to 100, with 100 being the best.

The term "deep blue emitting" has the ordinary meaning to one of ordinary skill in the art. In some embodiments, a material is "deep blue emitting" if it emits deep blue light. In some embodiments, deep blue light having the approximate CIE color coordinates (X=[0.14], Y=[0.08], CIE 1931).

Some embodiments provide a compound represented by the following formula:

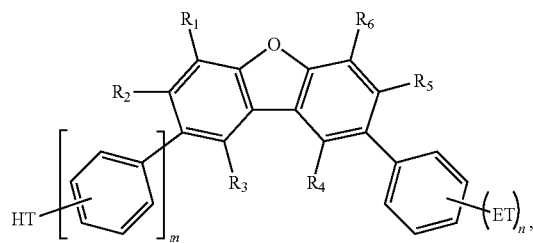

In this host compound formula, $R_1$, $R_2$, $R_3$, $R_4$, $R_5$ and $R_6$ can be independently selected from H, $C_1$-$C_3$ alkyl, and $C_{-3}$ perfluoroalkyl. HT can be selected from optionally substituted carbazoyl, optionally substituted phenylnaphthylamine, and optionally substituted diphenylamine, where m is 0 or 1. For example, HT can be selected from one of the following:

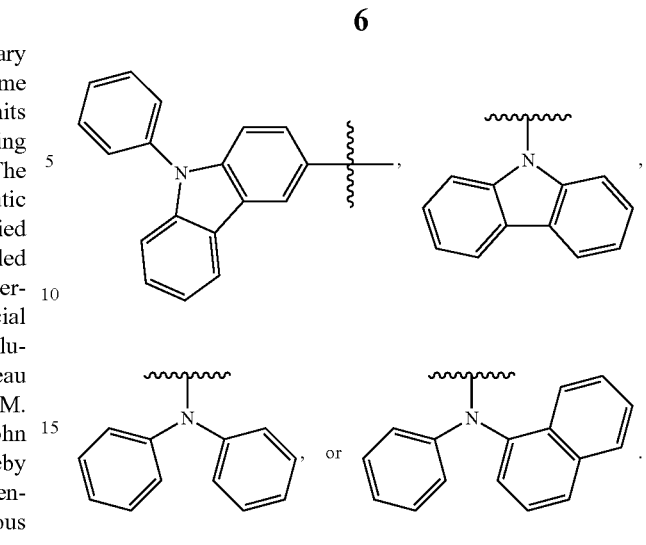

ET can be selected from optionally substituted benzimidazol-2-yl, optionally substituted benzothiazol-2-yl, optionally substituted benzoxazol-2-yl, optionally substituted 3,3'-bipyridin-5-yl, optionally substituted quinolin-8-yl, optionally substituted quinolin-5-yl, and optionally substituted quinoxalin-5-yl, where n is 1 or 2. For example, ET can be selected from one of the following:

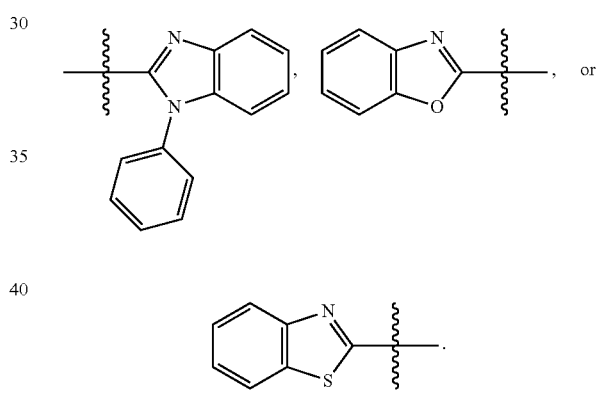

Some embodiments relate to compounds which can be selected from:

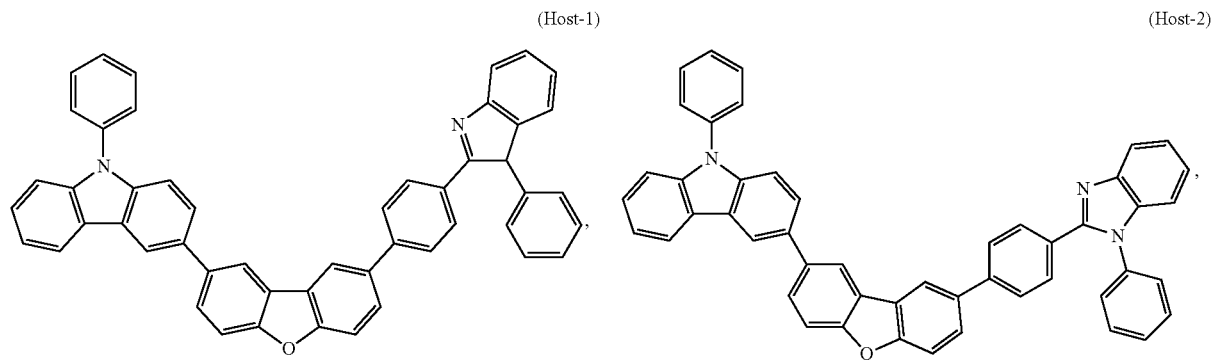

(Host-3)
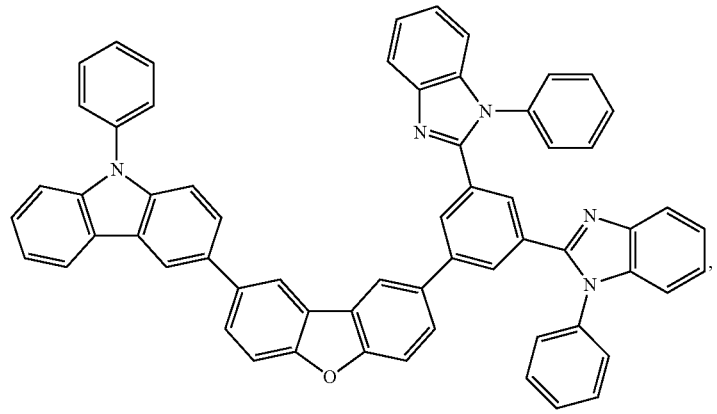
(Host-4)
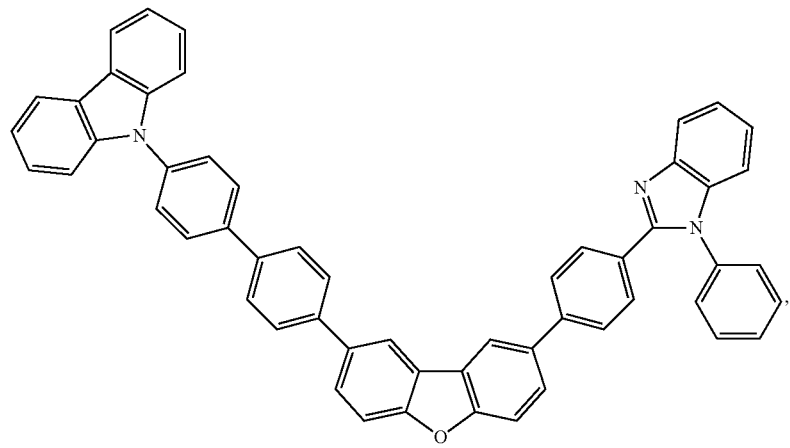
(Host-5) (Host-6)
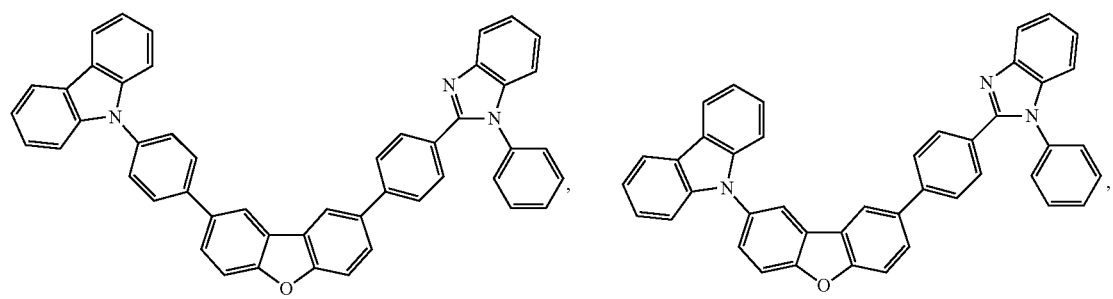
(Host-7) (Host-8)
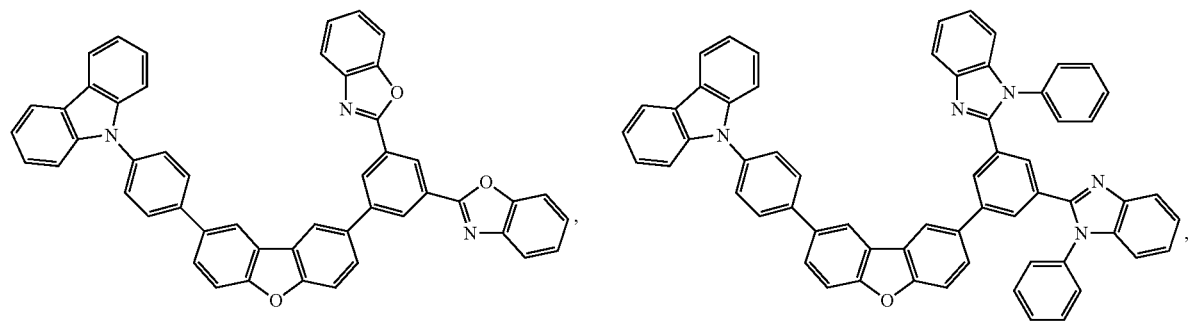

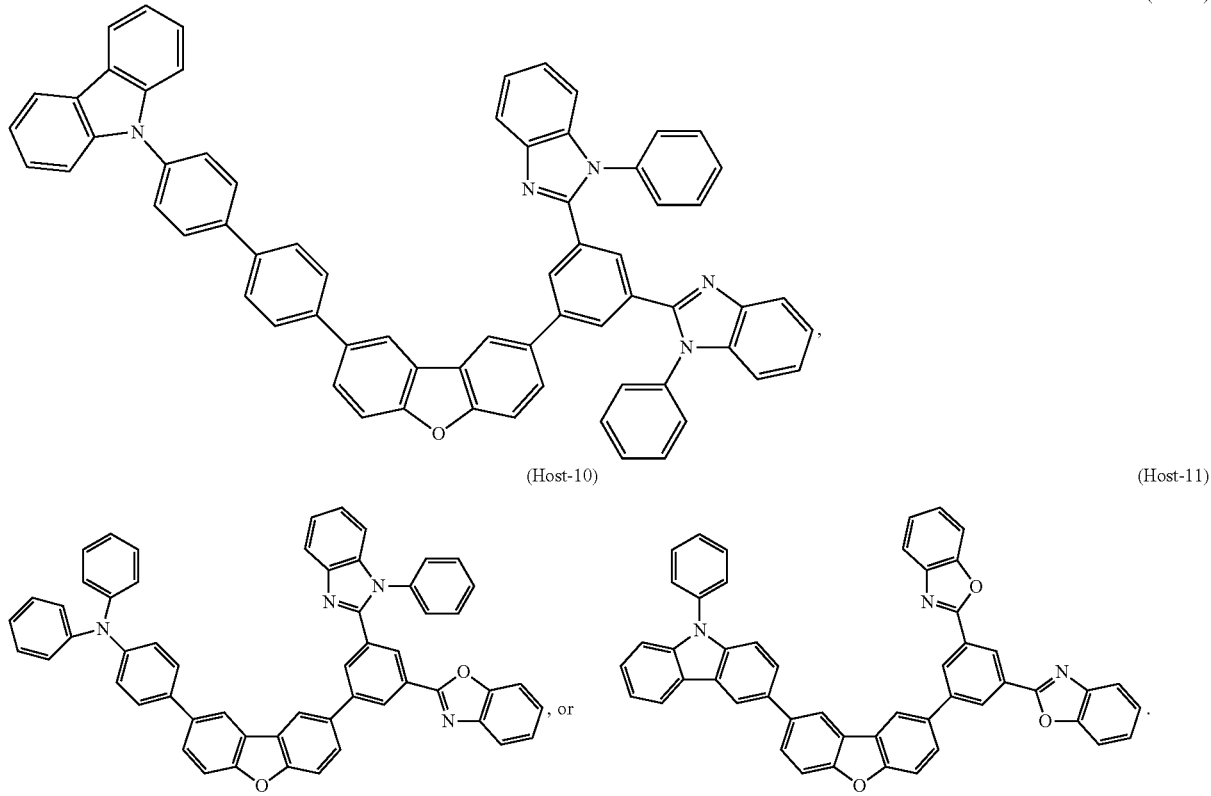

(Host-9)

(Host-10)

(Host-11)

Some embodiments include optionally substituted Host-1, optionally substituted Host-2, optionally substituted Host-3, optionally substituted Host-3, optionally substituted Host-5, optionally substituted Host-6, optionally substituted Host-7, optionally substituted Host-8, optionally substituted Host-9, optionally substituted Host-10, or optionally substituted Host-11.

Some embodiments include optionally substituted Host-1. Some embodiments include optionally substituted Host-2. Some embodiments include optionally substituted Host-3. Some embodiments include optionally substituted Host-3. Some embodiments include optionally substituted Host-5. Some embodiments include optionally substituted Host-6. Some embodiments include optionally substituted Host-7. Some embodiments include optionally substituted Host-8. Some embodiments include optionally substituted Host-9. Some embodiments include optionally substituted Host-10. Some embodiments include. Some embodiments include optionally substituted Host-11.

In some embodiments, a compound of any formula included herein, or an optionally substituted Host-1, Host-2, Host-3, Host-4, Host-5, Host-6, Host-7, Host-8, Host-9, Host-10, or Host-11, may have a highest occupied molecular orbital having an energy of about 5 eV to about 7 eV, about −5.5 eV to about 6 eV, about −5.5 eV to about −5.7 eV, or about 5.6 eV to about 5.7 eV.

In some embodiments, a compound of any formula included herein, or an optionally substituted Host-1, Host-2, Host-3, Host-4, Host-5, Host-6, Host-7, Host-8, Host-9, Host-10, or Host-11, may have a lowest unoccupied molecular orbital having an energy of about −2 eV to about −3 eV, about −2.1 eV to about −2.6 eV, about −2.1 eV to about −2.5 eV, about −2.1 eV to about −2.3 eV, or about −2.5 eV to about −2.6 eV.

In some embodiments, a compound of any formula included herein, or an optionally substituted Host-1, Host-2, Host-3, Host-4, Host-5, Host-6, Host-7, Host-8, Host-9, Host-10, or Host-11, may have a triplet energy of about 2 eV to about 3 eV, about 2.5 eV to about 2.7 eV, about 2.5 eV to about 2.6 eV, or about 2.6 eV to about 2.7 eV.

In some embodiments, a compound of any formula included herein, or an optionally substituted Host-1, Host-2, Host-3, Host-4, Host-5, Host-6, Host-7, Host-8, Host-9, Host-10, or Host-11, may have a glass transition temperature of about 100° C. to about 200° C., about 140° C. to about 180° C., about 160° C. to about 180° C., or about 140° C. to about 160° C.

In some embodiments, the compounds described may be used as an emissive compound, as an ambipolar host in an organic light-emitting diode emissive layer, or both. In some embodiments, the compounds described may be used in emissive elements of organic light emitting diode (OLED) devices. In some embodiments, the compounds disclosed herein may provide well balanced hole-transport and electron-transport mobility, which may lead to a simpler device structure with high quantum efficiency and low turn-on voltage. For example in some embodiments, the organic light-emitting diode or device incorporating the presently described compounds may not have a hole-transporting layer or an emissive layer. In some embodiments, these compounds may have high electrochemical stability, high thermal stability, a high glass transition temperature ($T_g$), and high photostability. Thus, these compounds may provide an OLED device with a longer lifetime than existing OLED devices.

The compounds and compositions described herein can be incorporated into light-emitting devices in various ways. For example, an embodiment provides a light-emitting device comprising: an anode layer made up of a high work function metal, a cathode layer made up of a low work function metal, and a light-emitting layer positioned between the anode layer and cathode layer. The light-emitting device may be configured so that the anode can transfer holes to the light-emitting layer and the cathode can transfer electrons to the light-emitting layer. The light-emitting layer contains the compounds and/or compositions disclosed herein.

An anode layer may comprise a conventional material such as a metal, mixed metal, alloy, metal oxide or mixed metal oxide, or a conductive polymer. Examples of suitable metals include the metals in Groups 10, 11, and 12 transition metals. If the anode layer is to be light-transmitting, mixed-metal oxides of Groups 12, 13 and 14 metals or alloys thereof, such as zinc oxide, tin oxide, indium zinc oxide or indium-tin-oxide may be used. The anode layer may include an organic material such as polyaniline, e.g., as described in "Flexible light-emitting diodes made from soluble conducting polymer," Nature, vol. 357, pp. 477-479 (11 Jun. 1992). Examples of suitable high work function metals include but are not limited to Au, Pt, indium-tin-oxide (ITO), or alloys thereof. In some embodiments, the anode layer can have thickness in the range of about 1 nm to about 1000 nm.

A cathode layer may include a material having a lower work function than the anode layer. Examples of suitable materials for the cathode layer include those selected from alkali metals of Group 1, 2, 11, 12, and 13 metals including rare earth elements, lanthanides and actinides, materials such as aluminum, indium, calcium, barium, samarium, and magnesium, and combinations thereof. Li-containing organo-metallic compounds, LiF, and Li$_2$O may also be deposited between the organic layer and the cathode layer to lower the operating voltage. Suitable low function metals include but are not limited to Al, Ag, Mg, Ca, Cu, Mg/Ag, LiF/Al, CsF, CsF/Al or alloys thereof. In some embodiments, the cathode layer can have thickness in the range of about 1 nm to about 1000 nm.

The amount of the compounds disclosed herein in the light-emitting composition can vary. In the described embodiment the compound disclosed herein is approximately 90% by weight of the light-emitting layer. However, the amount of the compound disclosed herein in the light-emitting layer may be in the range of from about 1% to 100% by weight of the light-emitting layer. In some embodiments, the mass of the electroluminescent compound may be about 0.1% to about 10%, about 1% to about 5%, or about 3% of the mass of the emissive layer.

The thickness of the light-emitting layer may vary. In one embodiment, the light-emitting layer thickness is about 30 nm. However, this is not intended to be limiting, the light-emitting layer can have a thickness in the range of about 5 nm to 200 nm.

The compounds and compositions described herein may be useful in an emissive layer without requiring any additional hole-transport or electron-transport materials. Thus, in some embodiments, the light-emitting layer consists essentially of an electroluminescent compound and a compound disclosed herein. In some embodiments, the light-emitting layer may comprise at least one hole-transport material or electron-transport material in addition to a compound disclosed herein.

In some embodiments, a hole-transport material may comprise at least one of an aromatic-substituted amine, a carbazole, a polyvinylcarbozole (PVK), e.g. poly(9-vinyl-carbozole); N,N'-bis(3-methylphenyl)N,N'-diphenyl-[1,1'-biphenyl]-4,4'-diamine (TPD); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; 1,1-bis(4-bis(4-methylyphenyl)aminophenyl)cyclohexane; 2,9-dimethyl-4,7-diphenyl-1,10-phenanthroline; 3,5-bis(4-tert,butyl-phenyl)-4-phenyl[1,2,4] triazole; 3,4,5-triphenyl-1,2,3-triazole; 4,4',4"-tris(N-naphthylen-2-yl)-N-phenylamino)triphyenylamine (MTDATA); 4,4'-bis[N-(naphthyl-N-phenyl-amino]biphenyl (NPB); 4,4'-bis[N,N'-(3-tolyl)amino]-3,3'-dimethylbiphenyl (HMTPD); 4,4'-N'-dicarbazolebiphenyl (CBP); 1,3-N,N-dicarbazole-benzene (mCP); poly(9-vinylcarbazole) (PVK); a benzidine; a phenylenediamine; a phyhalocyanine metal complex; a polyacetylene; a polythiophene; a triphenylamine an oxadiazole; copper phthalocyanine; N,N',N"-1,3, 5-tricarbazoloylbenzene (tCP); N,N'-bis(4-butylphenyl)-N, N'-bis(phenyl)benzidine; and the like.

In some embodiments, an electron-transport material may comprise at least one of 2-(4-biphenylyl)-5-(4-tert-butylphenyl)-1,3,4,oxadiazole (PBD); 1,3-bis(N,N-t-butylphenyl)-1, 3,4-oxadiazole (OXD-7); 1,3-bis[2-(2,2'-bipyridine-6-yl)-1, 3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidiazolyl)benzene; 1,3-bis[2-(2,2'-bipyridine-6-yl)-1,3,4-oxadiazol-5-yl]benzene (BPY-OXD); 3-phenyl-4-(1' naphthyl)-5-phenyl-1,2,4-triazole (TAZ); and 1,3,5-tris [2-N-phenylbenzimidazol-z-yl]benzene (TPBI). In one embodiment the electron transport layer may be aluminum quinolate (Alq$_3$), PBD, phenanthroline, quinoxaline, TPBI, or a derivative or a combination thereof.

In some embodiments, the device comprises no electron-transport or hole-transport layer. In some embodiments, the device consists essentially of the anode layer, the cathode layer, and the light-emitting layer. In other embodiments, the light-emitting device may further comprise a hole-transport layer disposed between the anode and the light-emitting layer. The hole-transport layer may comprise at least one hole-transport material. Suitable hole-transport materials may include those listed above in addition to any others known to those skilled in the art.

In some embodiments, the light-emitting device may further comprise an electron-transport layer disposed between the cathode and the light-emitting layer. The electron-transport layer may comprise at least one electron-transport material. Suitable electron-transport materials include those listed above as well as any others known to those skilled in the art.

If desired, additional layers may be included in the light-emitting device. These additional layers may be an electron injection layer (EIL), a hole blocking layer (HBL), an exciton blocking layer (EBL), and/or a hole injection layer (HIL). In addition to separate layers, some of these materials may be combined into a single layer.

In some embodiments, the light-emitting device can include an electron injection layer between the cathode layer and the light-emitting layer. A number of suitable electron injection materials are known to those skilled in the art. Examples of suitable material(s) that can be included in the electron injection layer include but are not limited to, an optionally substituted compound selected from the following: Alq$_3$; PBD; phenanthroline; quinoxaline; TPBI a triazine; a metal chelate of 9-hydroxyquinoline such as tris(8-hydroxyqunioliate) aluminum; and a metal thioxinoid compound such as bis(8-quinolinethiolato) zinc. In one embodiment, the electron injection layer may be a derivative or combination of the above listed materials.

In some embodiments, the device can include a hole-blocking layer, e.g., between the cathode and the light-emitting layer. Various suitable hole-blocking materials than can be included in the hole-blocking layer are known to those skilled in the art. Suitable hole-blocking material(s) include but are not limited to, an optionally substituted compound selected from the following: BCP; 3,4,5,triphenyl-1,2,4-triazole; 3,5-bis(4-tert-butyl-phenyl)-4-phenyl-[1,2,4]triazole; 2,9-dimethyl-4,7-diphenly-1,10-phenanthroline; and 1,1-bis(4-bis (methylphenyl)aminophenyl)-cyclohexane.

In some embodiments, the light-emitting device can include an exciton blocking layer, e.g., between the light-emitting layer and the anode. In an embodiment, the band gap of the material(s) that comprise an exciton blocking layer may be large enough to substantially prevent the diffusion of excitons. A number of suitable exciton blocking materials that can be included in an exciton blocking layer are known to those skilled in the art. Examples of material(s) that can compose an exciton blocking layer include an optionally substituted compound selected from the following: Alq$_3$; PB; CBP; BCP; and any other materials that have a large enough band gap to substantially prevent the diffusion of excitons.

In some embodiments, the light-emitting device can include a hole-injection layer, e.g., between the light-emitting layer and the anode. Various suitable hole-injection materials than can be included in the hole injection layer are known to those skilled in the art. Exemplary hole-injection material(s) may include an optionally substituted compound selected from the following: a polythiopene derivative such as poly(3,4-ethyenedioxythiophene) (PEDOT)/polystyrene (PSS); a benzidine derivative such as N,N,N',N'-tetraphenylbenzidine; poly(N,N'-bis(4-butylphenyl)-N,N'-bis(phenyl)benzidine); a tripenylamine or phenylenediamine derivative such as N,N'-bis(4-methylphenyl)-N,N'-bis(phenyl)-1,4-phenylenediamine, 4,4',4"tris(naphthylen-2-yl)-N-phenylamino)triphenylamine; an oxadiazole derivative such as 1,3-bis(5-(4-diphenylamino)phenyl-1,3,4-oxadiazol-2-yl) benzene; a polyacetylene derivative such as poly(1,2-bis-benzylthio-acetylene); and a phthalocyanine metal complex derivative such as phthalocyamine copper. Hole-injection materials, while still being able to transport holes, may have a hole mobility substantially less than the hole mobility of conventional hole-transport materials.

The emissive compositions may be prepared by adapting methods known in the art for other emissive compositions. For example, the emissive compositions may be prepared by dissolving or dispersing the electroluminescent compound (including any compound described herein) and any host (including any compound described herein), if present, in a solvent and depositing the composition on the appropriate layer of the device. The liquid may be a single phase, or may comprise one or more additional solid or liquid phases dispersed in it. The solvent may then be allowed to evaporate, or the solvent may be removed via heat or vacuum, to provide an emissive composition. Alternatively, an electroluminescent compound may be melted, or added to a molten or liquid host material (if present). The molten composition may then be applied as a layer into the device, and allowed to solidify to provide a viscous liquid or solid emissive composition layer.

Light-emitting devices comprising the compounds disclosed herein can be fabricated using techniques known in the art, as informed by guidance provided herein. For example, a glass substrate can be coated with a high work functioning metal such as ITO which can act as an anode. After patterning the anode layer, a light-emitting layer that includes at least a compound disclosed herein, and optional electroluminescent compound, can be deposited on the anode. The cathode layer, comprising a low work functioning metal, can then be deposited, e.g., vapor evaporated, onto the light-emitting layer. If desired, the device can also include an electron transport/injection layer, a hole blocking layer, a hole injection layer, an exciton blocking layer and/or a second light-emitting layer that can be added to the device using techniques known in the art, as informed by the guidance provided herein.

An example of a configuration of a device comprising a compound as described herein is shown in FIG. 1. The device comprises the following layers in the order given: An ITO anode 10; a PEDOT:PSS hole-injection layer 15; a 4,4',4"-tri (N-carbazolyl)triphenylamine (TCTA) hole-transport layer 20; an light-emitting layer comprising an electroluminescent compound and one of the host compounds described herein 25; a TPBI electron-transport layer 30; an Al/LiF cathode 35; and a glass cap 40.

In some embodiments, the OLED may be configured by a wet process such as a process that comprises at least one of spraying, spin coating, drop casting, inkjet printing, screen printing, etc. Some embodiments provide a composition which may be a liquid suitable deposition onto a substrate. The liquid may be a single phase, or may comprise one or more additional solid or liquid phases dispersed in it. The liquid typically comprises a light-emitting compound, a host material disclosed herein, and a solvent.

The following are examples of some methods that may be used to prepare compounds and devices as described herein. Each compound of note is labeled in bold on each of the figures presented. For example, compound 1 is labeled 1 on the figure, compound 2 is labeled 2, etc. In addition, the synthesis of said compound is described in the examples below.

Example 1

Organic Synthesis

Example 1.1

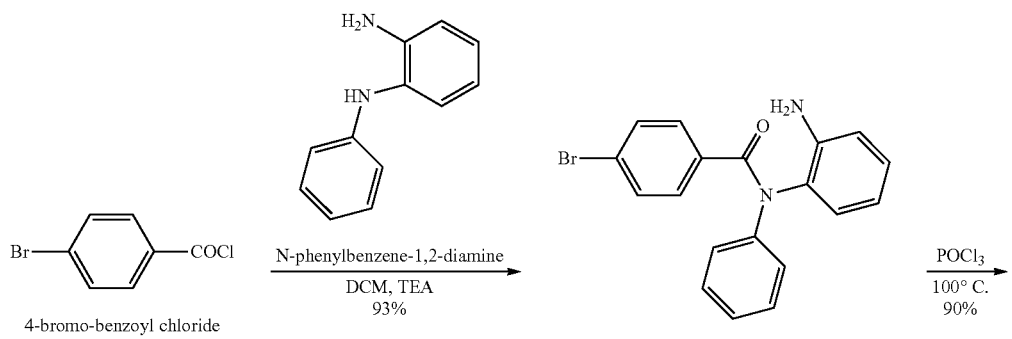

1

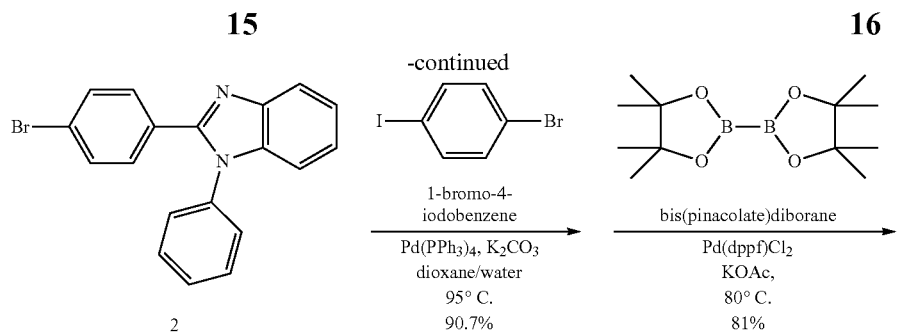
2
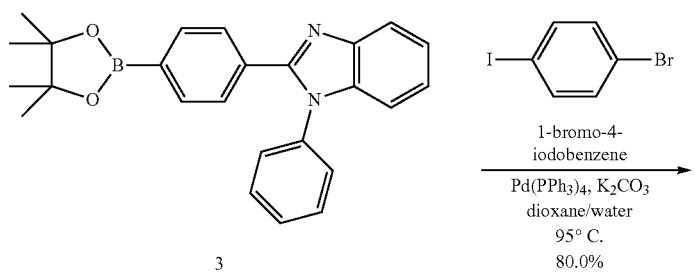
3
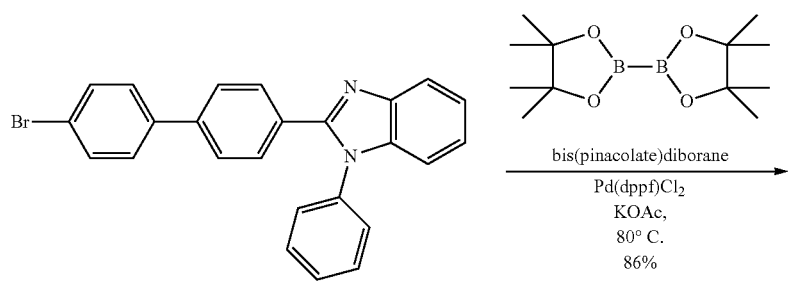
4
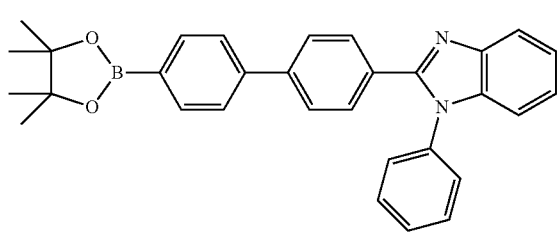
5
Example 1.1.1
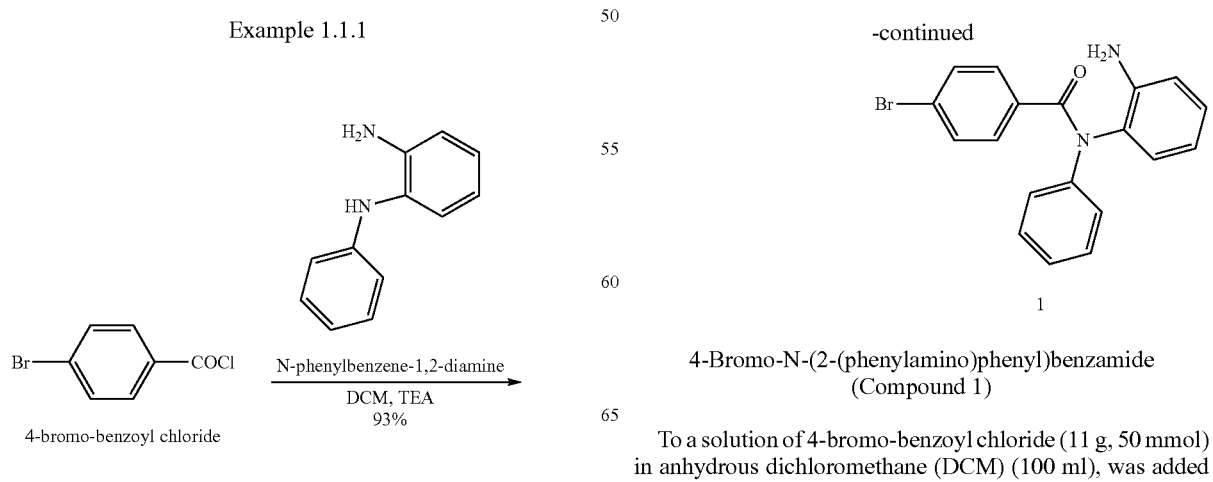
4-Bromo-N-(2-(phenylamino)phenyl)benzamide
(Compound 1)
To a solution of 4-bromo-benzoyl chloride (11 g, 50 mmol) in anhydrous dichloromethane (DCM) (100 ml), was added N-phenylbenzene-1,2-diamine (10.2 g, 55 mmol), then triethylamine (TEA) (17 mL, 122 mmol) slowly. The whole was stirred at room temperature (RT) overnight. Filtration gave a white solid (1, 6.5 g). The filtrate was worked up with water (300 mL), then extracted with DCM (300 mL) three times. The organic phase was collected and dried over MgSO$_4$, concentrated and recrystallized in DCM/hexanes to give another portion of white solid 1 (10.6 g). Total amount of product 1 is 17.1 g, in 93% yield.

Example 1.1.2

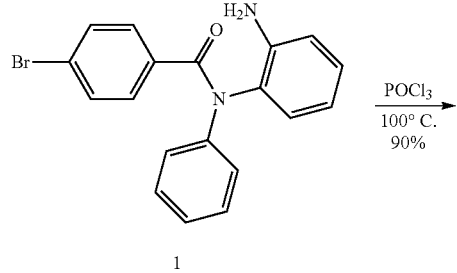

2-(4-bromophenyl)-1-phenyl-1H-benzo[d]imidazole (Compound 2)

To a suspension of amide 1 (9.6 g, 26 mmol) in anhydrous 1,4-dioxane (100 mL) was added phosphorus oxychloride (POCl$_3$) (9.2 mL, 100 mmol) slowly. The whole was then heated at about 100° C. overnight. After cooling to RT, the mixture was poured into ice (200 g) with stirring. Filtration, followed by recrystallization in DCM/hexanes gave a pale grey solid 2 (8.2 g, in 90% yield).

Example 1.1.3

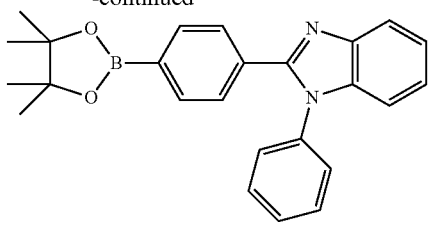

1-phenyl-2-(4-(4,4,5,5-tetramethyl-1,3,2-dioxaborolan-2-yl)phenyl)-1H-benzo[d]imidazole (Compound 3)

A mixture of Compound 2 (0.70 g, 2 mmol), bis(pinacolate)diborane (0.533 g, 2.1 mmol), bis(diphenylphosphino)ferrocene]dichloropalladium (Pd(dppf)Cl$_2$) (0.060 g, 0.08 mmol) and anhydrous potassium acetate (KOAc) (0.393 g, 4 mmol) in 1,4-dioxane (20 ml) was heated at about 80° C. under argon overnight. After cooling to RT, the whole was diluted with ethyl acetate (80 mL) then filtered. The solution was absorbed on silica gel, then purified by column chromatography (hexanes/ethyl acetate 5:1 to 3:1) to give a white solid 3 (0.64 g, in 81% yield).

Example 1.1.4

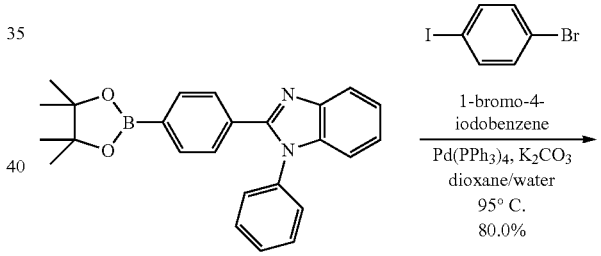

2-(4'-bromo-[1,1'-biphenyl]-4-yl)-1-phenyl-1H-benzo[d]imidazole (Compound 4)

A mixture of Compound 3 (4.01 g, 10.1 mmol), 1-bromo-4-iodobenzene (5.73 g, 20.2 mmol), Pd(PPh$_3$)$_4$ (0.58 g, 0.5 mmol) and potassium carbonate (4.2 g, 30 mmol) in dioxane/water (60 mL/10 mL) was degassed and heated at about 95° C. overnight. After being cooled to RT, the mixture was poured into ethyl acetate (250 mL), washed with brine, dried over Na$_2$SO$_4$, then loaded on silica gel, purified by flash column (hexanes to hexanes/ethyl acetate 4:1) to give a light yellow solid washed with methanol and dried in air (3.39 g, in 80% yield).

Example 1.1.5

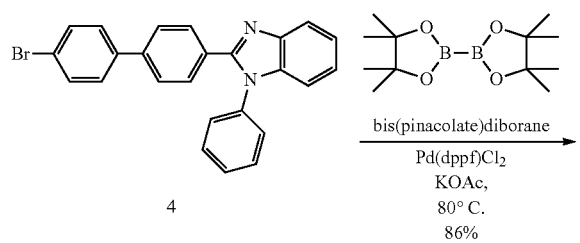

1-phenyl-2-(4'-(4,4,5,5-tetramethyl-1,3,2-dioxaborolan-2-yl)-[1,1'-biphenyl]-4-yl)-1H-benzo[d]imidazole (Compound 5)

A mixture of Compound 4 (1.2 g, 2.82 mmol), bis(pinacolate)diborane (0.72 g, 2.82 mmol), bis(diphenylphosphino)ferrocene]dichloropalladium (Pd(dppf)Cl$_2$) (0.10 g, 0.14 mmol) and anhydrous potassium acetate (KOAc) (2.0 g, 20 mmol) in 1,4-dioxane (45 ml) was heated at about 80° C. under argon overnight. After cooling to RT, the whole was diluted with ethyl acetate (150 mL) then filtered. The solution was absorbed on silica gel, then purified by column chromatography (hexanes/ethyl acetate 5:1 to 3:1) to give a white solid 5 (1.14 g, in 86% yield).

Example 1.2

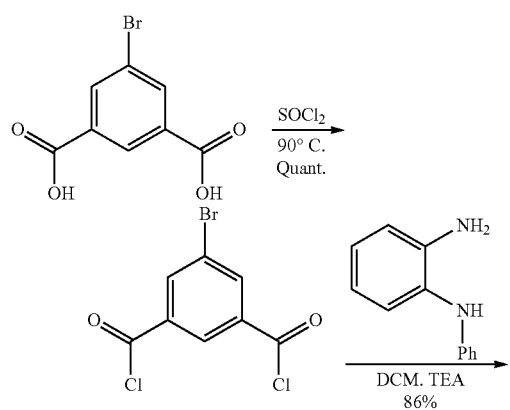

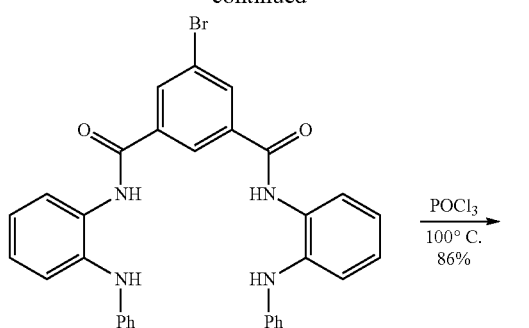

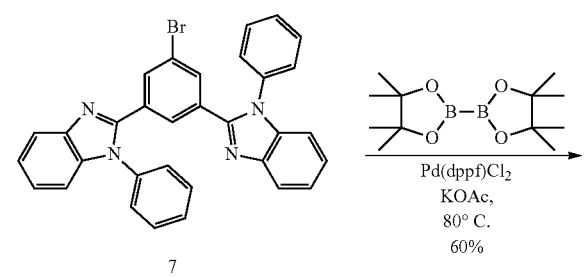

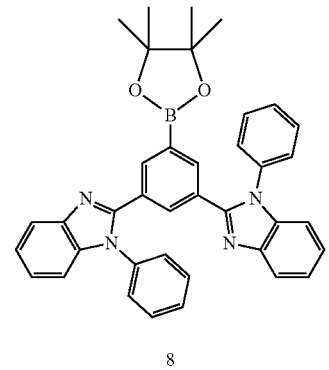

Example 1.2.6

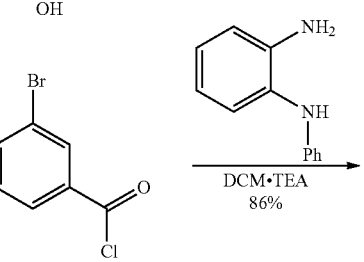

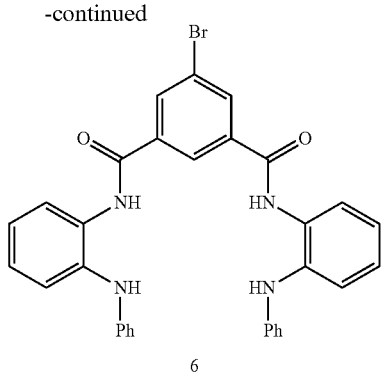

5-Bromo-N1,N3-bis(2-(phenylamino)phenyl)isophthalamide (Compound 6)

A mixture of 5-bromoisophthalic acid (15 g, 61.2 mmol) in thionyl chloride (60 mL) with 0.2 mL DMF was heated to reflux for overnight under argon. After removal of the excess thionyl chloride under reduced pressure, the remaining liquid was dissolved in anhydrous dichloromethane (200 mL). To the solution, N-phenyl-o-phenyldiamine (22.5 g, 122 mmol) was added, then triethylamine (22.2 mL, 160 mL) was added slowly with ice-bath cooling. The mixture was stirred overnight with slowly warming up the ice-bath to room temperature. The resulting suspension was diluted with dichloromethane (200 mL), filtered and washed with dichloromethane to give an off-white solid (30.3 g, yield: 86%). Confirmed by LCMS (APCI): calcd for $C_{32}H_{26}BrN_4O_2$ (M+H): 577. Found: 577.

Example 1.2.7

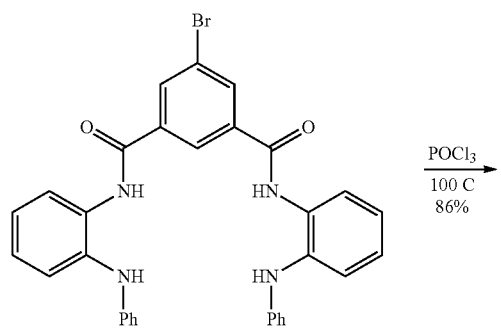

2,2'-(5-bromo-1,3-phenylene)bis(1-phenyl-1H-benzo[d]imidazole) (Compound 7)

To a suspension of the isophthalamide 6 (30 g, 52 mmol) in anhydrous dioxane (300 mL), POCl$_3$ (30.6 g, 0.2 mmol) was added slowly with water bath cooling. The mixture was heated at about 100° C. overnight with drying tube on top of the condenser. After cooled to room temperature, the mixture was poured into ice (300 g), then neutralized with Na$_2$CO$_3$, following by extraction with dichloromethane (600 mL) twice. The organic phase was collected and washed with brine, dried over Na$_2$SO$_4$, concentrated to 100 mL. To the mixture, acetonitrile (300 mL) was added and stirred, then filtered. The solid was collected and re-crystallized in dichloromethane/hexane to afford a white solid (18.88 g). The filtrate was purified by flash column (hexane to hexanes/ethyl acetate 9:1 to 4:1). The main fraction was collected and concentrated to give additional product, white solid (5.17 g). Total amount is 24.05 g, in 86% yield. Confirmed by LCMS (APCI): calcd for $C_{32}H_{22}BrN_4$ (M+H): 541. Found: 541.

Example 1.2.8

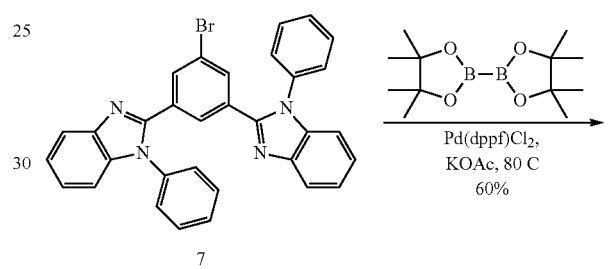

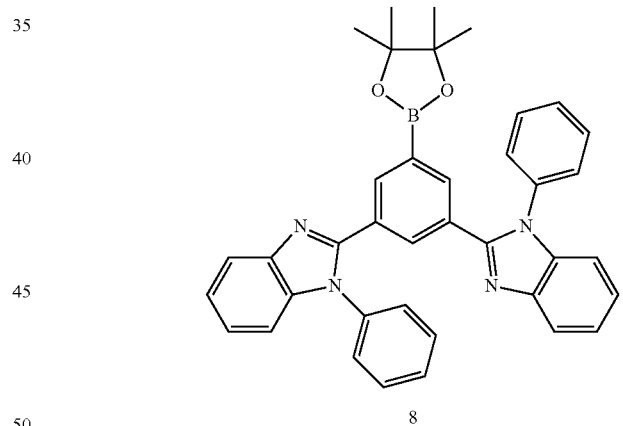

2,2'-(5-(4,4,5,5-tetramethyl-1,3,2-dioxaborolan-2-yl)-1,3-phenylene)bis(1-phenyl-1H-benzo[d]imidazole) (Compound 8)

A mixture of Compound 7 (10.0 g, 18.5 mmol), bis(pinacolate)diborane (5.0 g, 20 mmol), Pd(dppf)Cl$_2$ (0.5 g, 0.68 mmol) and potassium acetate (10.0 g, 0.10 mol) in anhydrous dioxane (300 mL) was degassed and heated at about 80° C. for 30 hours. The mixture was poured into ethyl acetate (300 mL), the organic phase was collected, washed with brine, dried over Na$_2$SO$_4$ and purified by flash column (hexanes/dichloromethane 7:3). The main fraction was collected and concentrated to afford a light yellow solid (6.58 g, in 60% yield). Confirmed by LCMS (APCI): calcd for $C_{38}H_{34}BN_4O_2$ (M+H): 589. Found: 589.

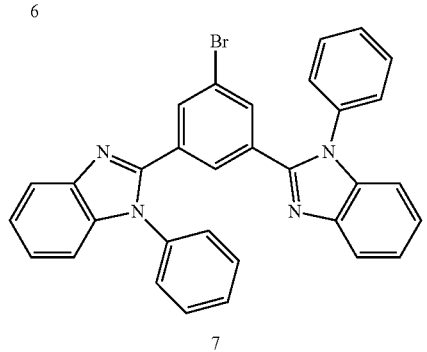

23
Example 1.3
Synthesis of Host-1
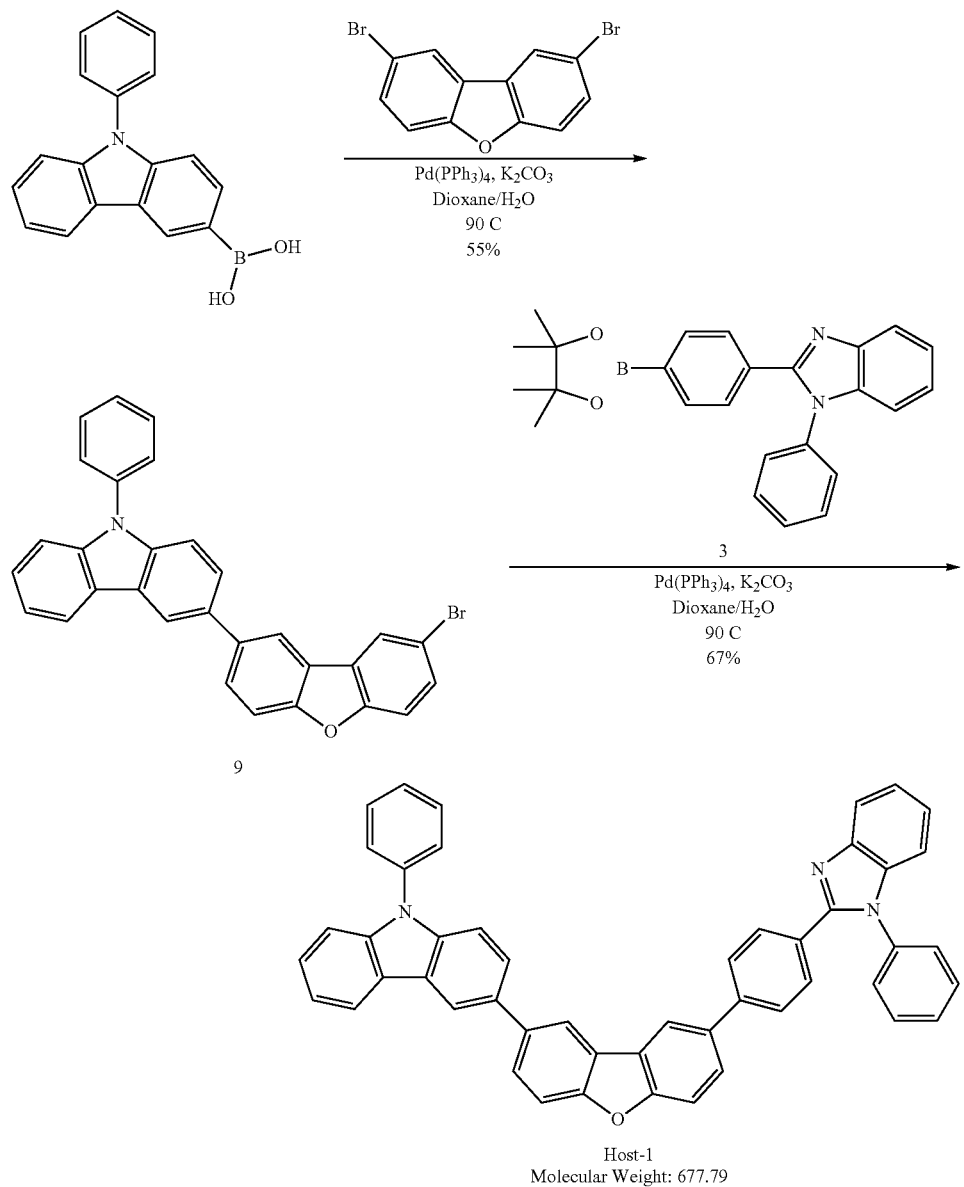
Host-1
Molecular Weight: 677.79
24
Example 1.3.9
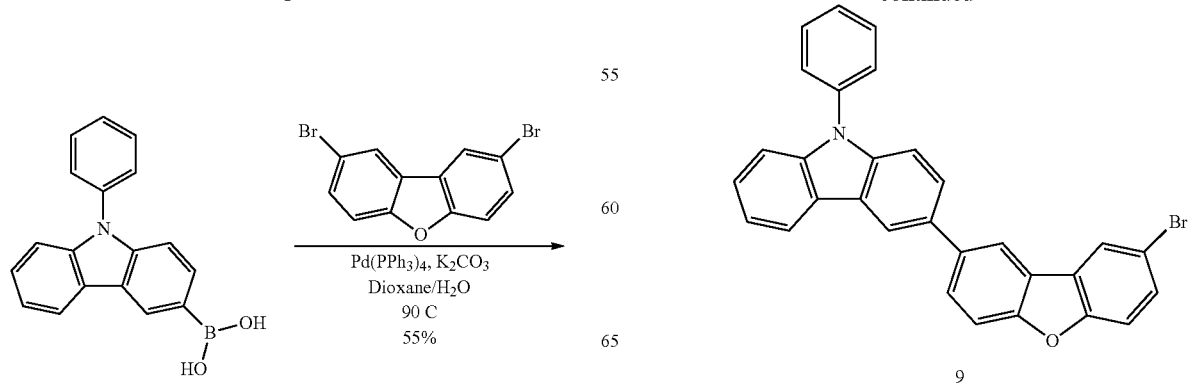
-continued

3-(8-bromodibenzo[b,d]furan-2-yl)-9-phenyl-9H-carbazole (Compound 9)

A mixture of 2,8-dibromodibenzo[b,d]furan (2.868 g, 10 mmol), (9-phenyl-9H-carbazol-3-yl)boronic acid (3.26 g, 10 mmol), Pd(PPh$_3$)$_4$ (0.30 g, 0.26 mmol) and potassium carbonate (4.1 g, 30 mmol) in dioxane/water (50 mL/10 mL) was degassed and heated at about 90° C. overnight. The resulting mixture was worked up with ethyl acetate/brine, dried over Na$_2$SO$_4$, purified by flash column (hexanes to hexanes/ethyl acetate 40:1). The desired fraction was collected and concentrated, filtration and dried in air to give a white solid (2.70 g, in 55% yield).

Example 1.3

Host-1

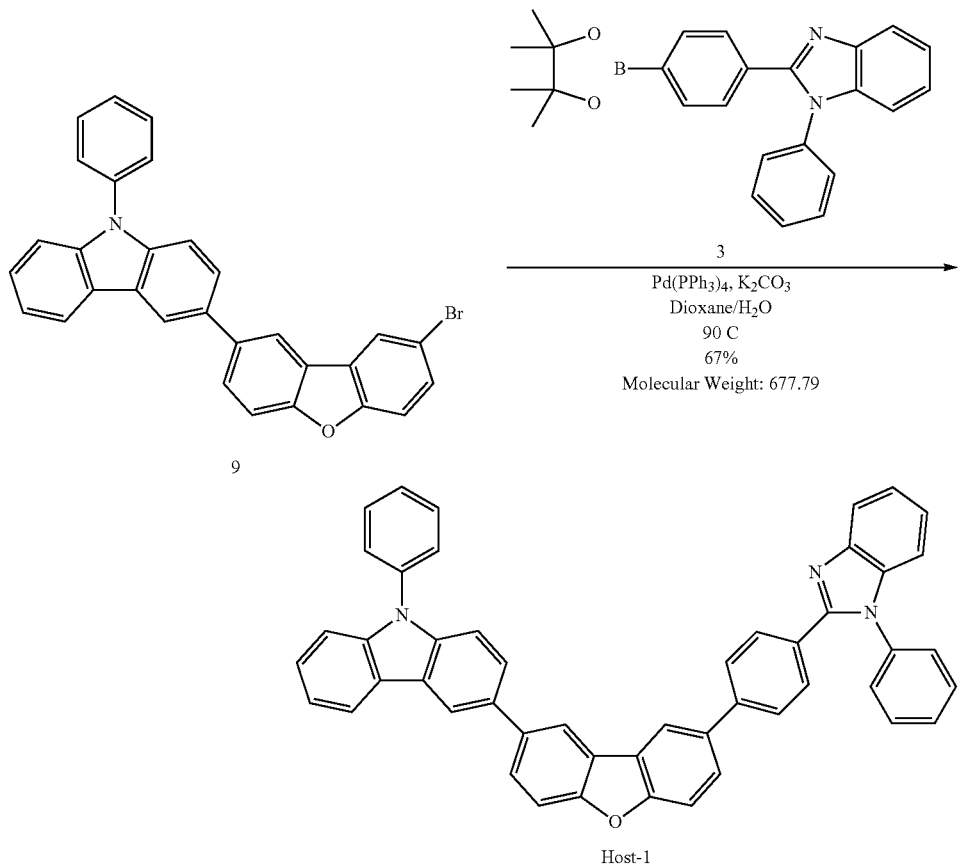

Host-1

A mixture of Compound 9 (2.0 g, 4.09 mmol), Compound 3 (1.62 g, 4.09 mmol), Pd(PPh$_3$)$_4$ (0.33 g, 0.286 mmol) and potassium carbonate (1.66 g, 12 mmol) in dioxane/water (55 mL/10 mL) was degassed and heated at about 90° C. overnight. The whole was diluted with ethyl acetate (150 mL), washed with brine, dried over Na$_2$SO$_4$, and purified by flash column (hexanes to hexanes/ethyl acetate 20:1 to hexanes/dichloromethane 1:1 to dichloromethane to dichloromethane/ethyl acetate 40:1 to 20:1). The major fraction was collected, concentrated, and recrystallized in dichloromethane/methanol to give a white solid (1.86 g, in 67% yield). LCMS (APCI): calcd for C$_{49}$H$_{32}$N$_3$O (M+H): 678. Found: 678.

Example 1.4
Synthesis of Host 2
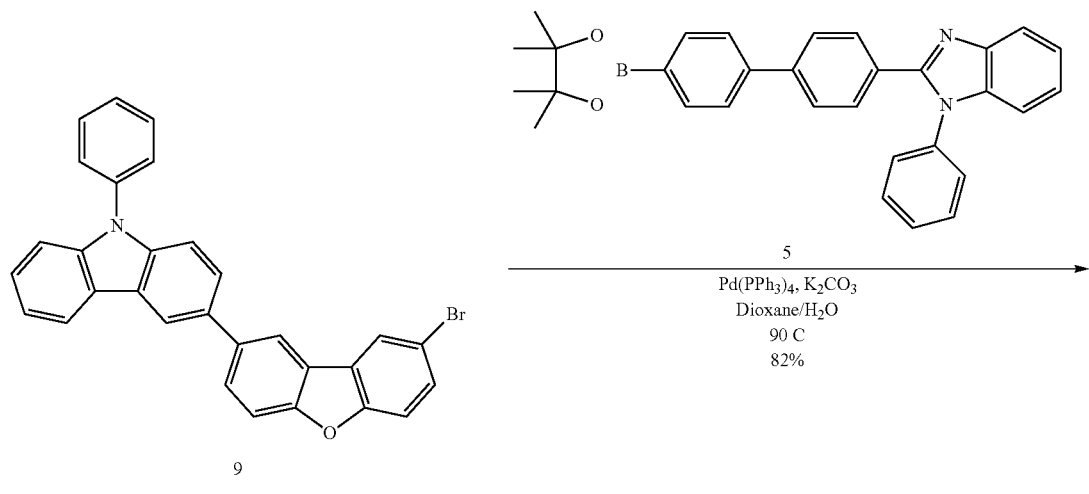
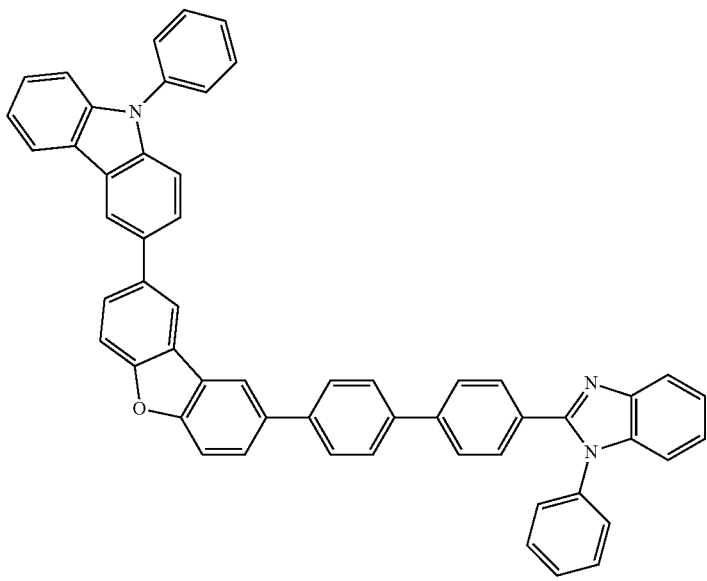
Host-2
A mixture of Compound 9 (1.6 g, 3.27 mmol), Compound 5 (1.545 g, 3.27 mmol), Pd(PPh$_3$)$_4$ (0.20 g, 0.17 mmol) and potassium carbonate (1.38 g, 10 mmol) in dioxane/water (55 mL/10 mL) was degassed and heated at about 90° C. for 6 hours. Large amount of white precipitate formed. Filtration and washed with methanol to give a white solid (2.0 g, in 81% yield). LCMS (APCI): calcd for C$_{55}$H$_{36}$N$_3$O (M+H): 754. Found: 754.

Example 1.5

Synthesis of Host 3

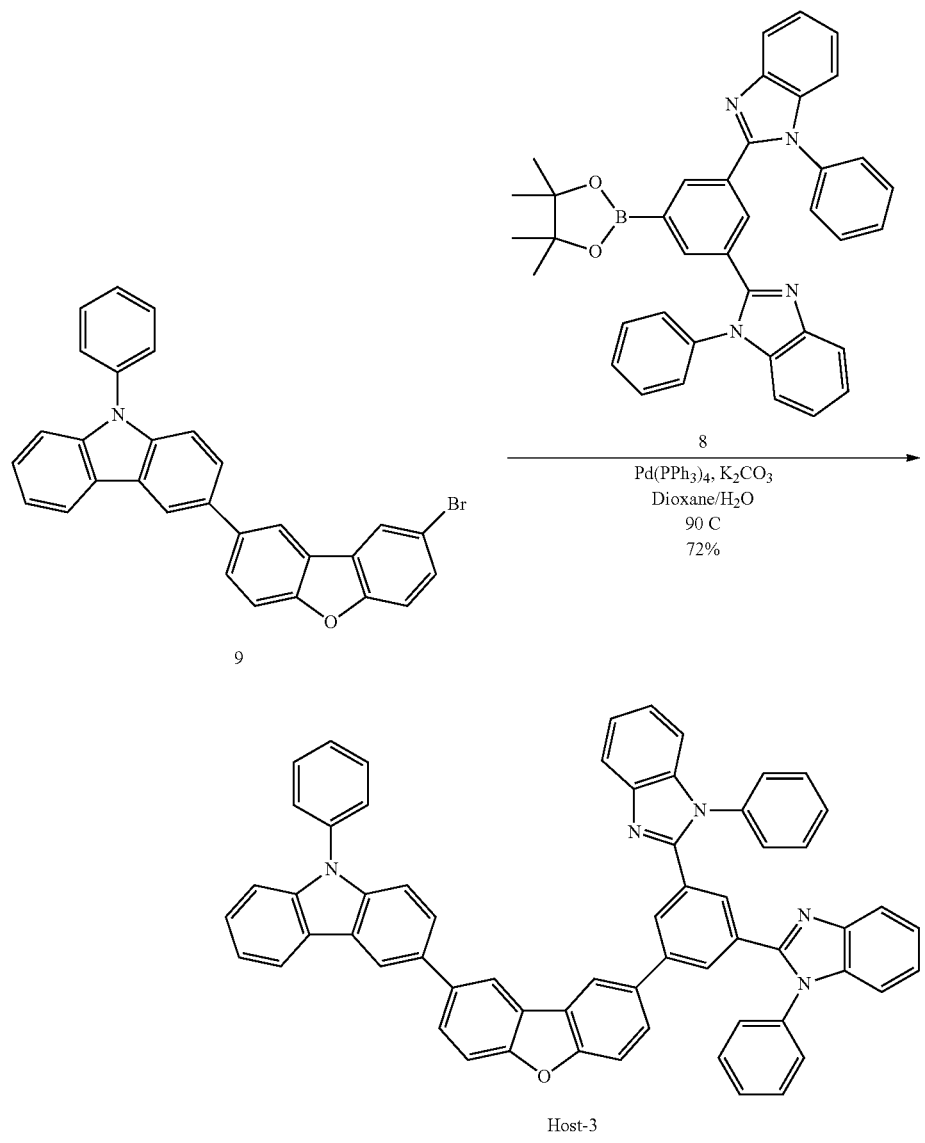

Host-3

A mixture of Compound 9 (0.87 g, 1.78 mmol), Compound 8 (1.05 g, 1.78 mmol), Pd(PPh$_3$)$_4$ (0.22 g, 0.19 mmol) and potassium carbonate (0.74 g, 5.36 mmol) in dioxane/water (50 mL/10 mL) was degassed and heated at about 90° C. overnight. The resulting mixture was worked up with ethyl acetate/brine, the organic phase was collected and dried over Na$_2$SO$_4$, purified by flash column (hexanes to hexanes/ethyl acetate 20:1 to dichloromethane to hexanes/ethyl acetate 9:1 to 7:3). The main fraction was collected, concentrated and filtration to give a white solid (1.11 g, in 72% yield). Confirmed by LCMS (APCI): calcd for C$_{62}$H$_{40}$N$_5$O (M+H): 870. Found 870.

Example 1.6

Synthesis of Host 4

Example 1.6.10

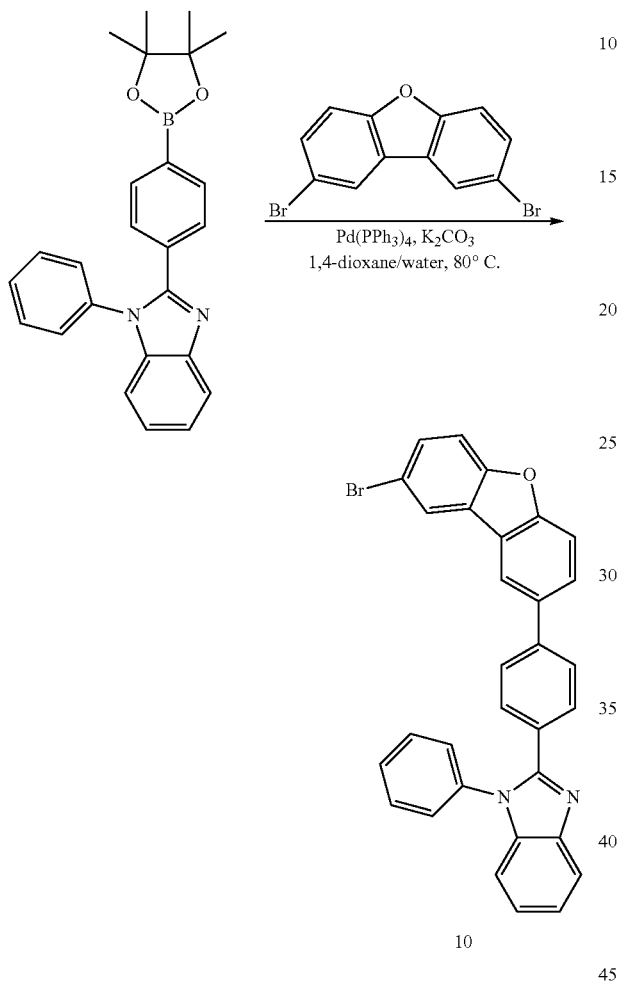

2-(4-(8-bromodibenzo[b,d]furan-2-yl)phenyl)-1-phenyl-1H-benzo[d]imidazole (Compound 10)

A mixture of 1-phenyl-2-(4-(4,4,5,5-tetramethyl-1,3,2-dioxaborolan-2-yl)phenyl)-1H-benzo[d]imidazole (4.42 g, 11.15 mmol), 2,8-dibromodibenzo[b,d]furan (4.03 g, 12.27 mmol), tetrakis(triphenylphosphine) palladium(0) (0.65 g, 0.56 mmol), potassium carbonate (4.62 g, 33.47 mmol), 1,4-dioxane (130.00 mL), and water (26.00 mL) was degassed with bubbling argon for 45 min at 50° C. The reaction mixture was then heated to 80° C. and was stirred overnight (16.5 hours), maintaining an argon atmosphere. Consumption of the starting material was confirmed by thin-layer chromatography and the reaction was cooled to room temperature. The product was extracted with ethyl acetate, dried, and purified by silica gel column chromatography with ethyl acetate in hexanes as the eluent. The product fractions were then dried and the product was collected to yield compound 10 (2.94 g, 51%). Confirmed by LCMS (APCI): calculated for $C_{31}H_{19}BrN_2O$ (M+H): 515. Found: 515.

Example 1.6

Host-4

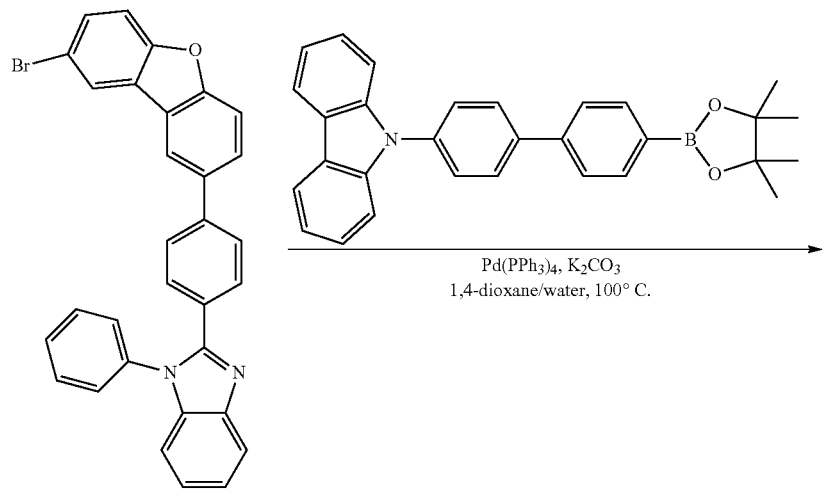

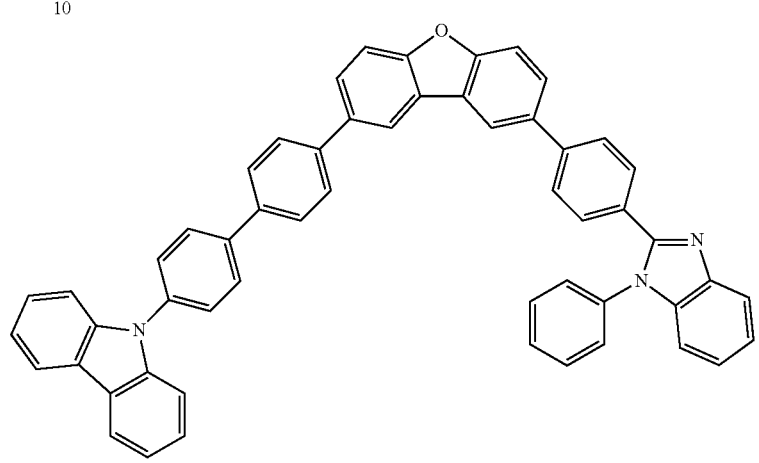

Host-4

Host-4: 9-(4'-(8-(4-(1-phenyl-1H-benzo[d]imidazol-2-yl)phenyl)dibenzo[b,d]furan-2-yl)-[1,1'-biphenyl]-4-yl)-9H-carbazole A mixture of Compound 10 (1.25 g, 2.43 mmol), 9-(4'-(4,4,5,5-tetramethyl-1,3,2-dioxaborolan-2-yl)-[1,1'-biphenyl]-4-yl)-9H-carbazole (1.123 g, 2.52 mmol), tetrakis(triphenylphosphine) palladium(0) (0.14 g, 0.12 mmol), potassium carbonate (1.00 g, 7.27 mmol), 1,4-dioxane (25.00 mL), and water (5.00 mL) was degassed with bubbling argon for 45 minutes at 50° C. The reaction was then heated to 100° C. and stirred overnight (17 hours), maintaining an argon atmosphere. The precipitated product was filtered (filtrate saved for later purification), dried, and purified by column chromatography, on a silica gel column, with acetone in hexanes as the eluent. The product fractions were then dried to yield Host-4 (1.09 g). On the filtrate from the initial filtration, the material was extracted with ethyl acetate, dried, and purified by column chromatography, with the same eluent as the first column. The product fractions were then dried and combined with the collected product from the first column to yield a total of 1.40 g (76.2%) of Host-4. Confirmed by LCMS (APCI): calculated for $C_{55}H_{35}N_3O$ (M+H): 754. Found: 754.

Example 1.7

Synthesis of Host 5

Example 1.7.11

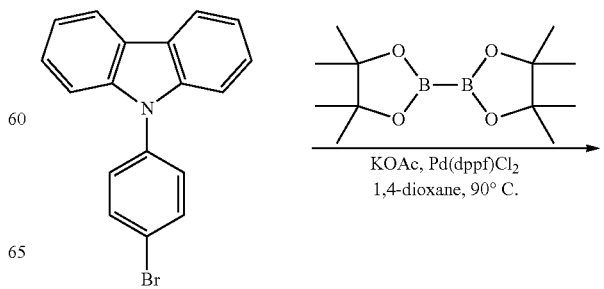

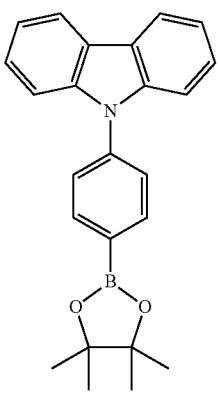

9-(4-(4,4,5,5-tetramethyl-1,3,2-dioxaborolan-2-yl)
phenyl)-9H-carbazole (Compound 11)

A mixture of 9-(4-bromophenyl)-9H-carbazole (7.39 g, 22.93 mmol), bis(pinacolato)diboron (6.40 g, 25.22 mmol), [1,1′-bis(diphenyl-phosphino)ferrocene]-dichloropalladium (II) (0.836 g, 1.15 mmol), potassium acetate (6.75 g, 68.78 mmol), and anhydrous 1,4-dioxane (125.00 mL) was degassed with bubbling argon for 1 hour at room temperature. The reaction was then heated to 80° C. and was stirred over two nights (46 hours), maintaining an argon atmosphere. Consumption of the starting material was confirmed by thin-layer chromatography and the reaction was cooled to room temperature. The product was then extracted with ethyl acetate, dried, and purified by silica gel column chromatography with dichloromethane in hexanes as the eluent. The product fractions were then dried to yield Compound 11 (4.63 g, 55%). Confirmed by LCMS (APCI): calculated for $C_{24}H_{24}BNO_2$ (M+H): 370. Found: 370

Example 1.7

Host-5

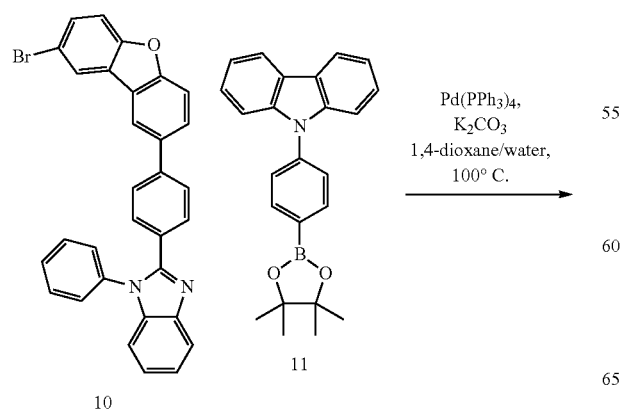

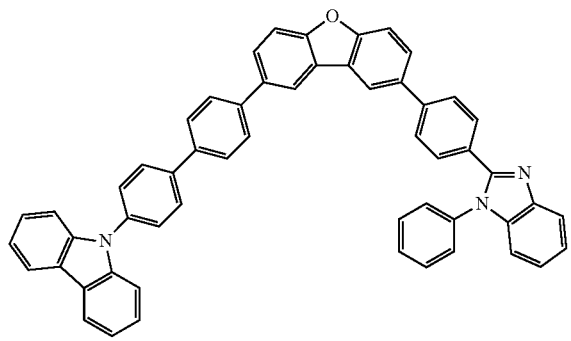

Host-5: 9-(4-(8-(4-(1-phenyl-1H-benzo[d]imidazol-2-yl)phenyl)dibenzo[b,d]furan-2-yl)phenyl)-9H-carbazole A mixture of Compound 10 (1.25 g, 2.43 mmol), Compound 11 (0.931 g, 2.52 mmol), tetrakis(triphenylphosphine)palladium(0) (0.14 g, 0.12 mmol), potassium carbonate (1.00 g, 7.27 mmol), 1,4-dioxane (25.00 mL), and water (5.00 mL) was degassed with bubbling argon for 45 minutes at 50° C. The reaction was then heated to 100° C. and stirred overnight (17 hours), maintaining an argon atmosphere. The precipitated product was filtered, dried, purified by silica gel column chromatography with acetone in hexanes as the eluent, and recrystallized from acetone/hexanes. The recrystallized product was collected to yield Host-5 (1.34 g, 82%). Confirmed by LCMS (APCI): calculated for $C_{49}H_{31}N_3O$ (M+H): 678. Found: 678.

Example 1.8
Synthesis of Host-6
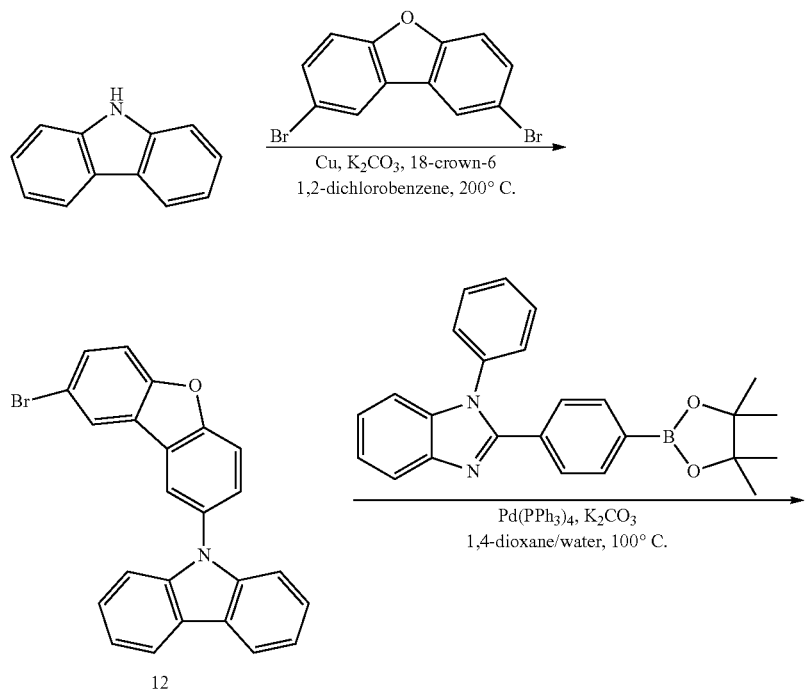
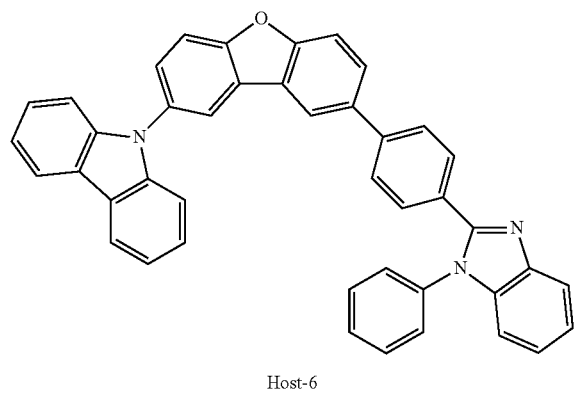
Host-6
Example 1.8.12
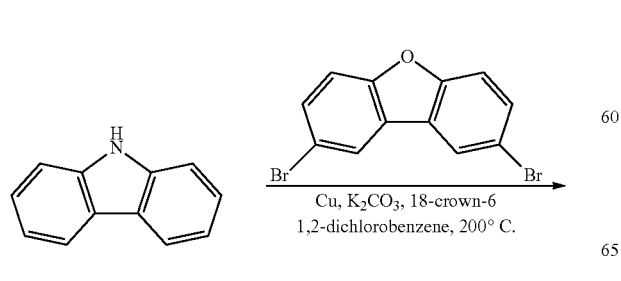
-continued
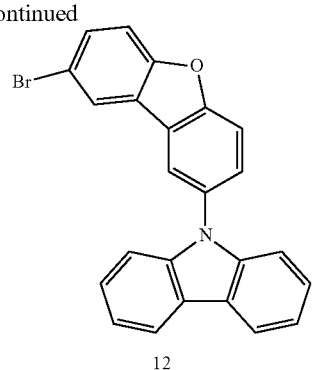

9-(8-bromodibenzo[b,d]furan-2-yl)-9H-carbazole (Compound 12)

A mixture of carbazole (1.15 g, 6.87 mmol), 2,8-dibromodibenzo[b,d]furan (4.48 g, 13.74 mmol), copper powder (0.30 g, 4.58 mmol), potassium carbonate (3.80 g, 27.50 mmol), 18-crown-6 (0.61 g, 2.29 mmol), and 1,2-dichlorobenzene (50 mL) was degassed with bubbling argon for 45 min at 50° C. The reaction mixture was then heated to 200° C. and was stirred overnight (45 hours), maintaining an argon atmosphere. Production of decoupled material was shown by LCMS and the reaction was cooled to room temperature. The mixture was filtered, and the filtrate was dried. The copper was removed by a short silica gel plug with dichloromethane as the eluent, and the product was purified by silica gel column chromatography with toluene in hexanes as the eluent. The product fractions were then dried and the product was collected to yield Compound 12 (0.861 g, 30%). Confirmed by LCMS (APCI): calculated for $C_{24}H_{14}BrNO$ (M+H): 412. Found: 412.

Example 1.8

Host-6

Host-6: 9-(8-(4-(1-phenyl-1H-benzo[d]imidazol-2-yl)phenyl)dibenzo[b,d]furan-2-yl)-9H-carbazole A mixture of Compound 12 (0.60 g, 1.46 mmol), 1-phenyl-2-(4-(4,4,5,5-tetramethyl-1,3,2-dioxaborolan-2-yl)phenyl)-1H-benzo[d]imidazole (0.60 g, 1.51 mmol), tetrakis(triphenylphosphine) palladium(0) (0.084 g, 0.072 mmol), potassium carbonate (0.60 g, 4.37 mmol), 1,4-dioxane (15.00 mL), and water (3.00 mL) was degassed with bubbling argon for 15 minutes. The reaction was then heated to 100° C. and stirred overnight (16.5 hours), maintaining an argon atmosphere. The precipitated product was filtered, dried, purified by silica gel column chromatography with acetone in hexanes as the eluent, and recrystallized from acetone/hexanes in a dry ice/isopropanol bath. The recrystallized product was collected to yield Host-6 (0.64 g, 73%). Confirmed by LCMS (APCI): calculated for $C_{43}H_{27}N_3O$ (M+H): 602. Found: 602.

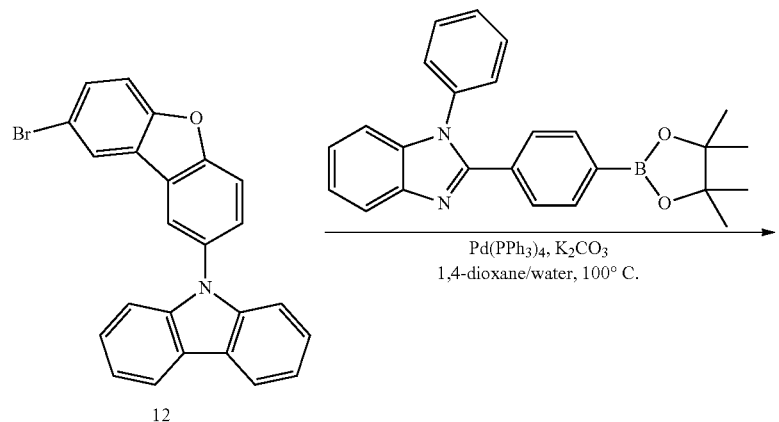

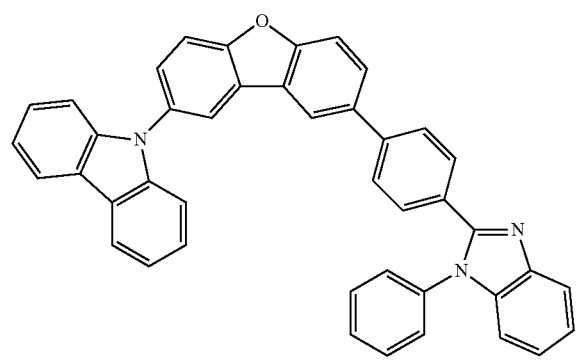

Host-6

Example 1.9
Synthesis of Host-7
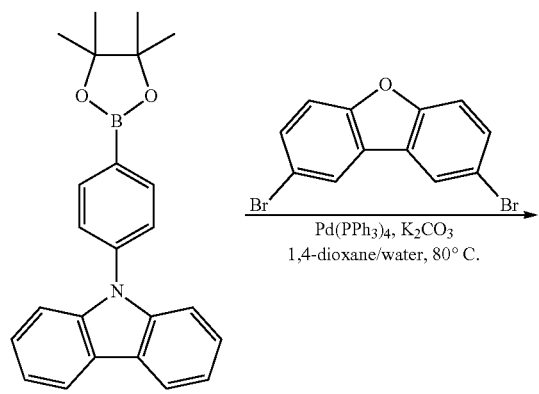
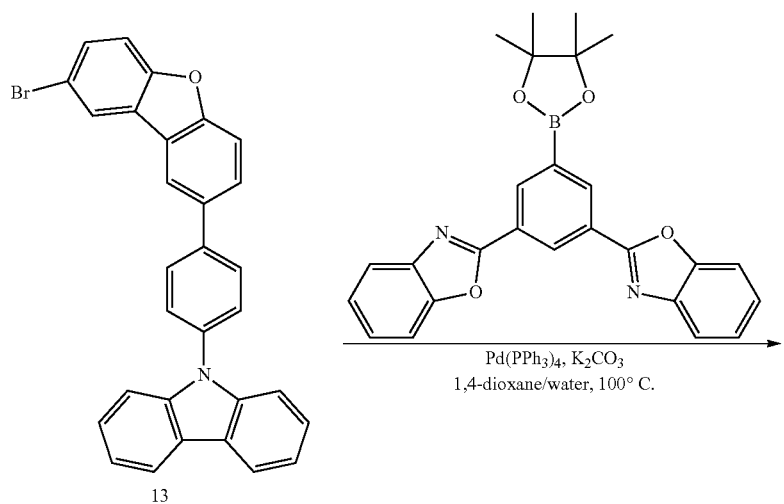
13
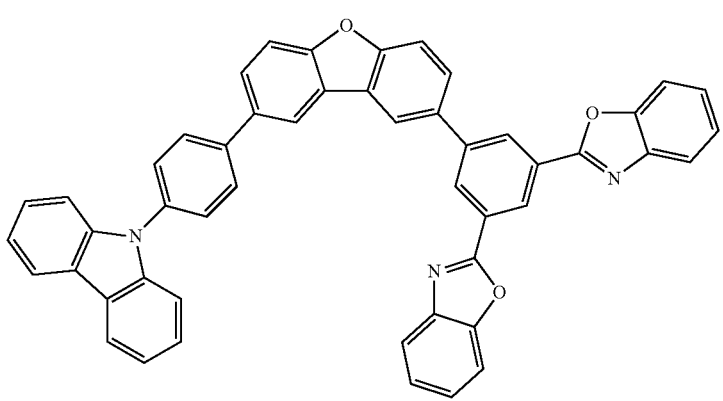
Host-7

Example 1.9.13

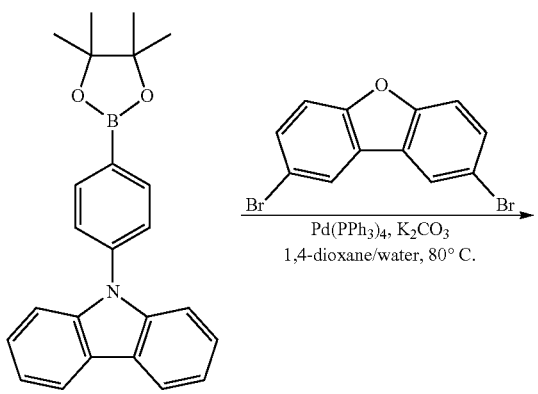

9-(4-(8-bromodibenzo[b,d]furan-2-yl)phenyl)-9H-carbazole (Compound 13)

A mixture of Compound 11 (2.00 g, 4.56 mmol), 2,8-dibromodibenzo[b,d]furan (2.60 g, 7.98 mmol), tetrakis(triphenylphosphine) palladium(0) (0.26 g, 0.23 mmol), potassium carbonate (1.892 g, 13.70 mmol), 1,4-dioxane (60.00 mL), and water (12.00 mL) was degassed with bubbling argon for 1 hour. The reaction mixture was then heated to 80° C. and was stirred overnight (16.5 hours), maintaining an argon atmosphere. Consumption of the starting material was confirmed by thin-layer chromatography and the reaction was cooled to room temperature. The product was extracted with dichloromethane, dried, and purified by silica gel column chromatography with dichloromethane in hexanes as the eluent. The product fractions were then dried and the product was collected to yield Compound 13 (1.57 g, 70%). Confirmed by LCMS (APCI): calculated for $C_{30}H_{18}BrNO$ (M+H): 488. Found: 488.

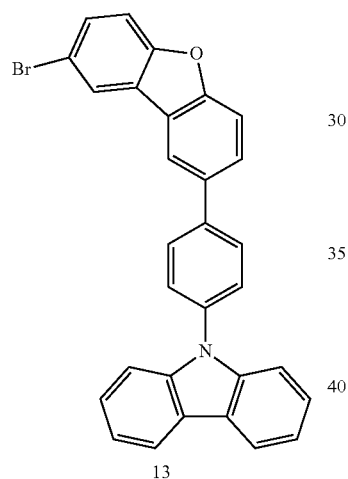

13

Example 1.9

Host-7

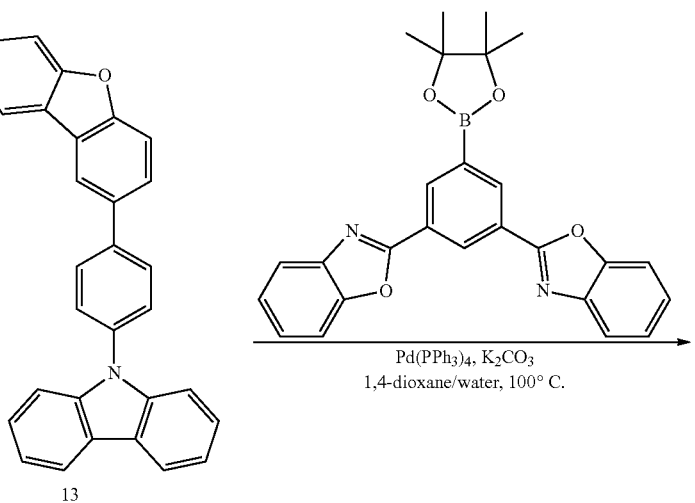

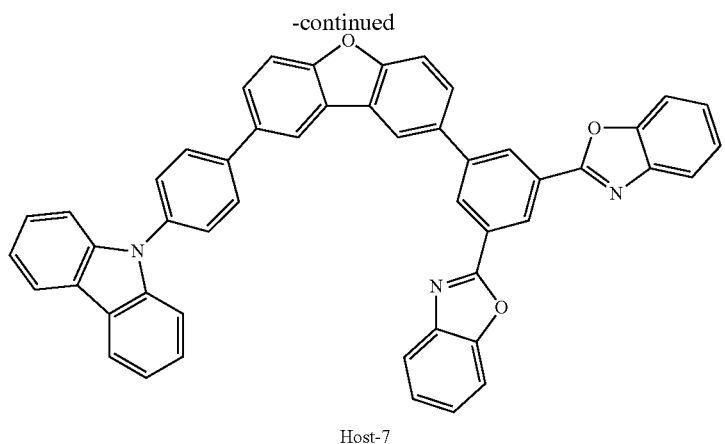

Host-7

Host-7: 2,2'-(5-(8-(4-(9H-carbazol-9-yl)phenyl)dibenzo[b,d]furan-2-yl)-1,3-phenylene)bis(benzo[d]oxazole)

A mixture of Compound 13 (1.00 g, 2.28 mmol), 2,2'-(5-(4,4,5,5-tetramethyl-1,3,2-dioxaborolan-2-yl)-1,3-phenylene)bis(benzo[d]oxazole) (1.159 g, 2.37 mmol), tetrakis(triphenylphosphine) palladium(0) (0.13 g, 0.11 mmol), potassium carbonate (0.95 g, 6.85 mmol), 1,4-dioxane (20.00 mL), and water (4.00 mL) was degassed with bubbling argon for 20 minutes at 45° C. The reaction was then heated to 100° C. and stirred overnight (16.5 hours), maintaining an argon atmosphere. The precipitated product was filtered, dried, and performed boiling ethyl acetate, chloroform, and methanol washes. The solid product was collected to yield Host-7 (0.75 g, 45%). Confirmed by LCMS (APCI): calculated for $C_{50}H_{29}N_3O_3$ (M+H): 720. Found: 720.

Example 1.10

Synthesis of Host-8

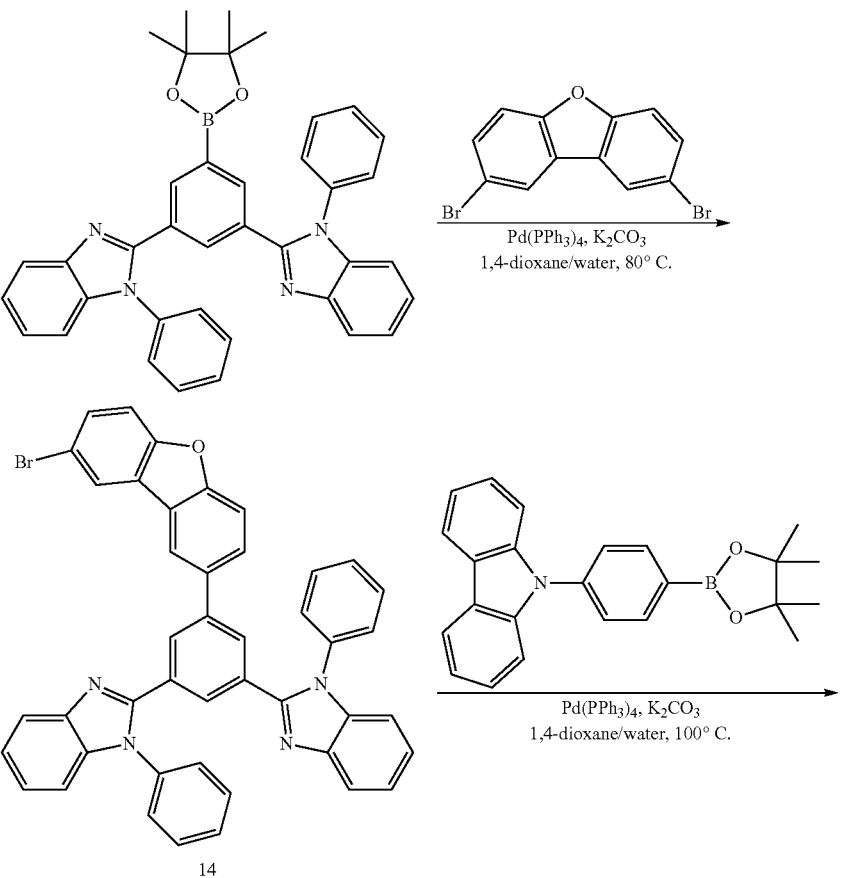

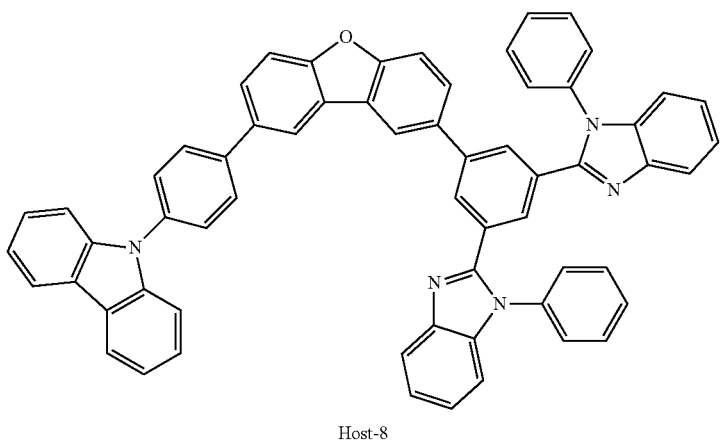

Host-8

Example 1.10.14

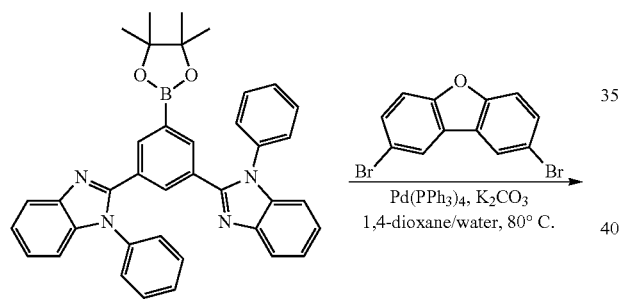

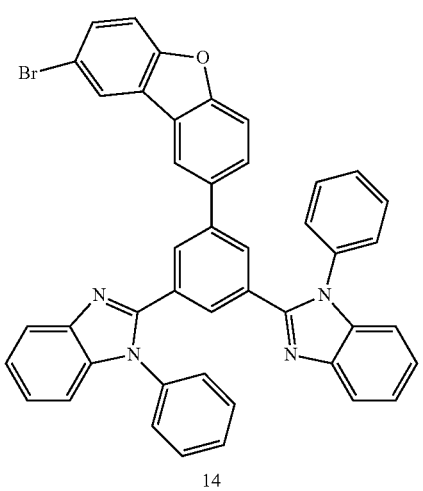

14

2,2'-(5-(8-bromodibenzo[b,d]furan-2-yl)-1,3-phenylene)bis(1-phenyl-1H-benzo[d]imidazole) (Compound 14)

A mixture of 2,2'-(5-(4,4,5,5-tetramethyl-1,3,2-dioxaborolan-2-yl)-1,3-phenylene)bis(1-phenyl-1H-benzo[d]imidazole) (3.00 g, 5.10 mmol), 2,8-dibromodibenzo[b,d]furan (1.83 g, 5.61 mmol), tetrakis(triphenylphosphine)palladium(0) (0.30 g, 0.26 mmol), potassium carbonate (2.11 g, 15.30 mmol), 1,4-dioxane (90.00 mL), and water (18.00 mL) was degassed with bubbling argon for 50 min. The reaction mixture was then heated to 80° C. and was stirred overnight (16.5 hours), maintaining an argon atmosphere. Consumption of the starting material was confirmed by thin-layer chromatography and the reaction was cooled to room temperature. The product was extracted with dichloromethane, dried, and purified by silica gel column chromatography with ethyl acetate in dichloromethane as the eluent. The product fractions were then dried and the product was collected to yield Compound 14 (2.00 g, 56%). Confirmed by LCMS (APCI): calculated for $C_{44}H_{27}BrN_4O$ (M+H): 707. Found: 707.

Example 1.10

Host-8

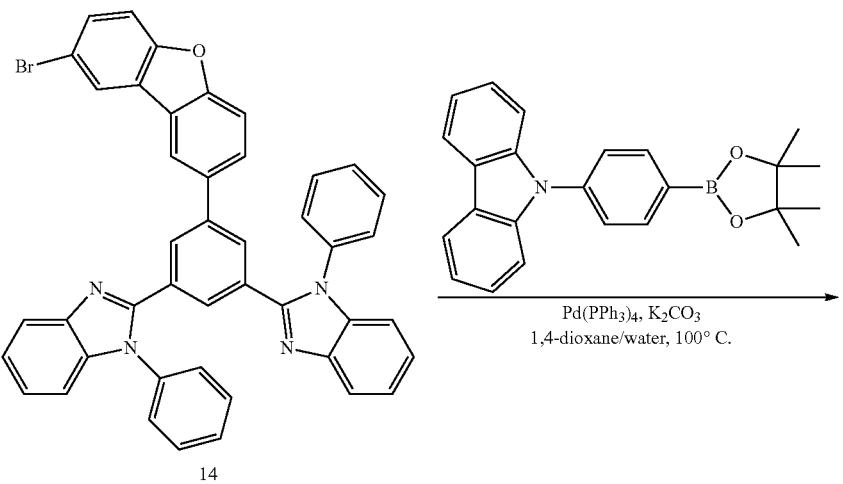

14

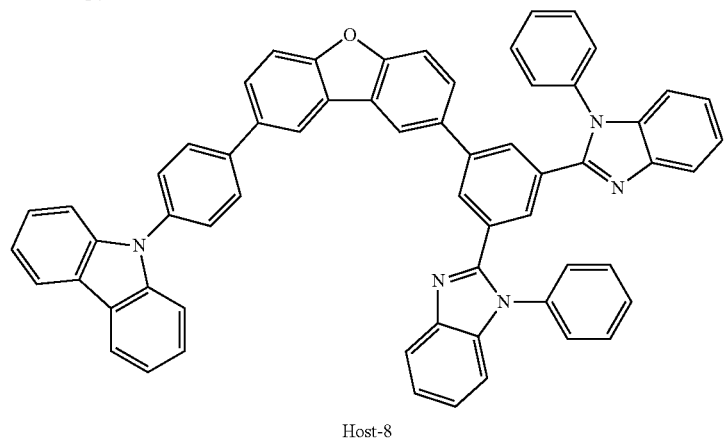

Host-8

Host-8: 9-(4-(8-(3,5-bis(1-phenyl-1H-benzo[d]imidazol-2-yl)phenyl)dibenzo[b,d]furan-2-yl)phenyl)-9H-carbazole A mixture of Compound 14 (1.30 g, 1.84 mmol), Compound 11 (0.75 g, 2.00 mmol), tetrakis(triphenylphosphine)palladium(0) (0.11 g, 0.092 mmol), potassium carbonate (0.76 g, 5.51 mmol), 1,4-dioxane (15.00 mL), and water (3.00 mL) was degassed with bubbling argon for 30 minutes. The reaction was then heated to 100° C. and stirred overnight (17.5 hours), maintaining an argon atmosphere. The product was extracted with dichloromethane, dried, purified by silica gel column chromatography with acetone in dichloromethane as the eluent, and recrystallized from methanol. The recrystallized product was collected to yield Host-8 (0.81 g, 51%). Confirmed by LCMS (APCI): calculated for $C_{62}H_{39}N_5O$ (M+H): 870. Found: 870.

Example 1.11
Synthesis of Host-9
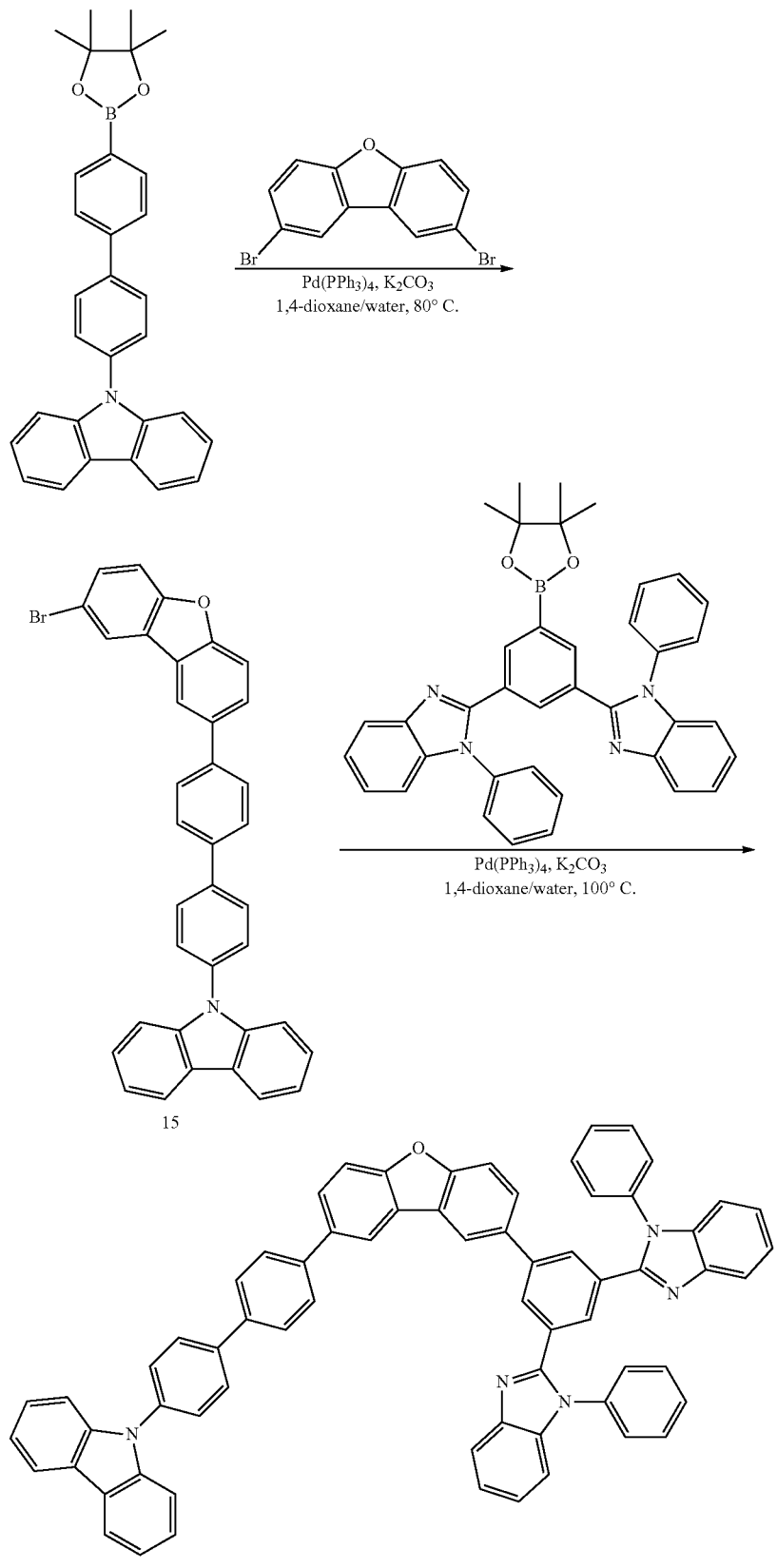
Host-9

Example 1.11.15

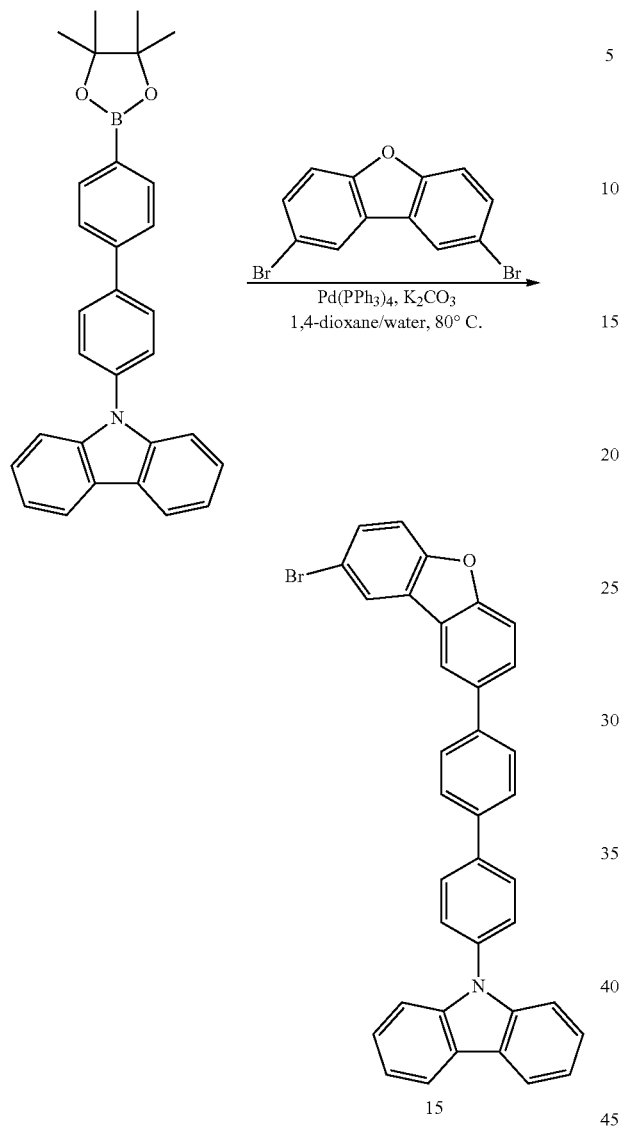

9-(4'-(8-bromodibenzo[b,d]furan-2-yl)-[1,1'-biphenyl]-4-yl)-9H-carbazole (Compound 15)

A mixture of 9-(4'-(4,4,5,5-tetramethyl-1,3,2-dioxaborolan-2-yl)-[1,1'-biphenyl]-4-yl)-9H-carbazole (1.75 g, 4.42 mmol), 2,8-dibromodibenzo[b,d]furan (2.52 g, 7.74 mmol), tetrakis(triphenylphosphine) palladium(0) (0.25 g, 0.22 mmol), potassium carbonate (1.83 g, 13.26 mmol), 1,4-dioxane (40.00 mL), and water (8.00 mL) was degassed with bubbling argon for 30 minutes. The reaction mixture was then heated to 80° C. and was stirred overnight (16.5 hours), maintaining an argon atmosphere. Consumption of the starting material was confirmed by thin-layer chromatography and the reaction was cooled to room temperature. The product was extracted with dichloromethane, dried, and purified by silica gel column chromatography with dichloromethane in hexanes as the eluent. The product fractions were then dried and the product was collected to yield Compound 15 (1.09 g, 44%). Confirmed by LCMS (APCI): calculated for $C_{36}H_{22}BrNO$ (M+H): 564. Found: 564.

Example 1.11

Host-9

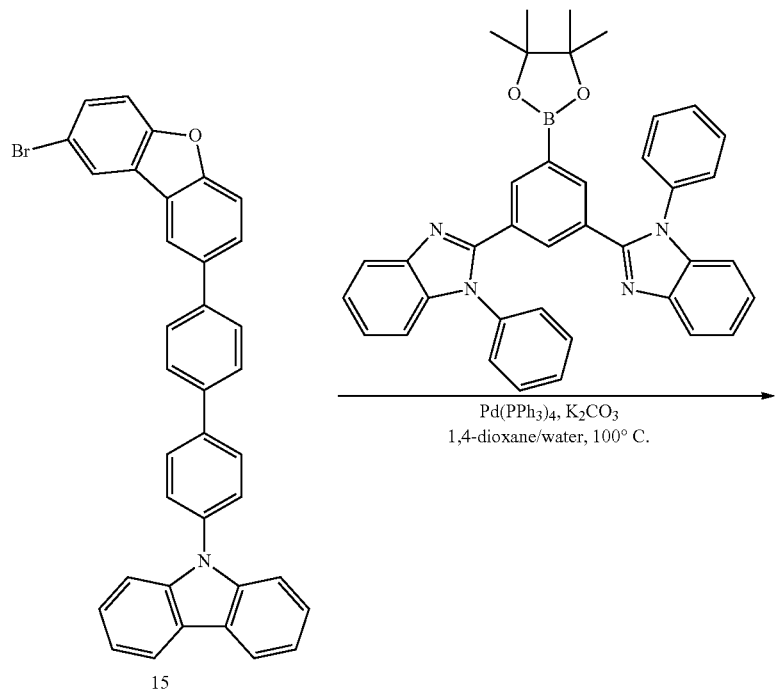

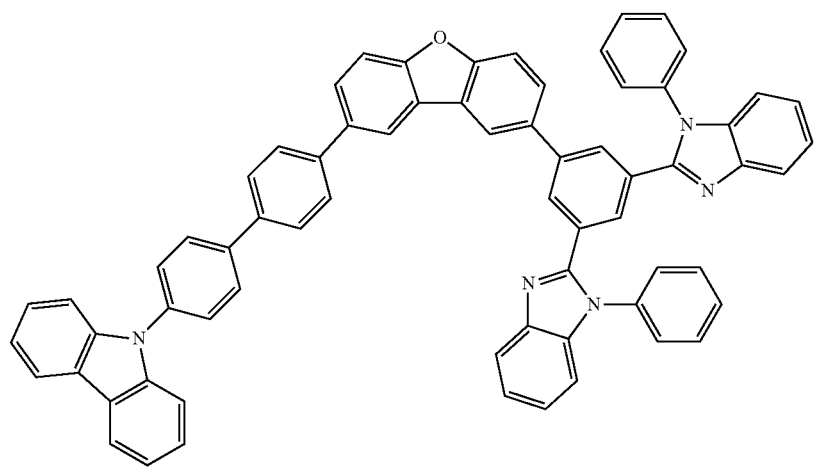

Host-9

Host-9: 9-(4'-(8-(3,5-bis(1-phenyl-1H-benzo[d]imidazol-2-yl)phenyl)dibenzo[b,d]furan-2-yl)-[1,1'-biphenyl]-4-yl)-9H-carbazole A mixture of Compound 15 (1.00 g, 1.78 mmol), 2,2'-(5-(4,4,5,5-tetramethyl-1,3,2-dioxaborolan-2-yl)-1,3-phenylene)bis(1-phenyl-1H-benzo[d]imidazole) (1.15 g, 1.95 mmol), tetrakis(triphenylphosphine) palladium(0) (0.10 g, 0.089 mmol), potassium carbonate (0.74 g, 5.32 mmol), 1,4-dioxane (20.00 mL), and water (4.00 mL) was degassed with bubbling argon for 30 minutes. The reaction was then heated to 100° C. and stirred overnight (16.5 hours), maintaining an argon atmosphere. The product was extracted with dichloromethane, dried, purified by silica gel column chromatography with acetone in dichloromethane as the eluent, and recrystallized from methanol. The recrystallized product was collected to yield Host-9 (1.34 g, 80%). Confirmed by LCMS (APCI): calculated for $C_{68}H_{43}N_5O$ (M+H): 946. Found: 946.

Example 1.12
Synthesis of Host-10
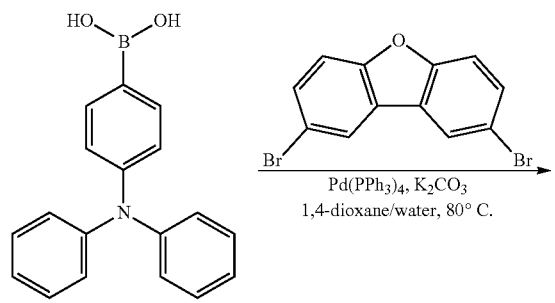
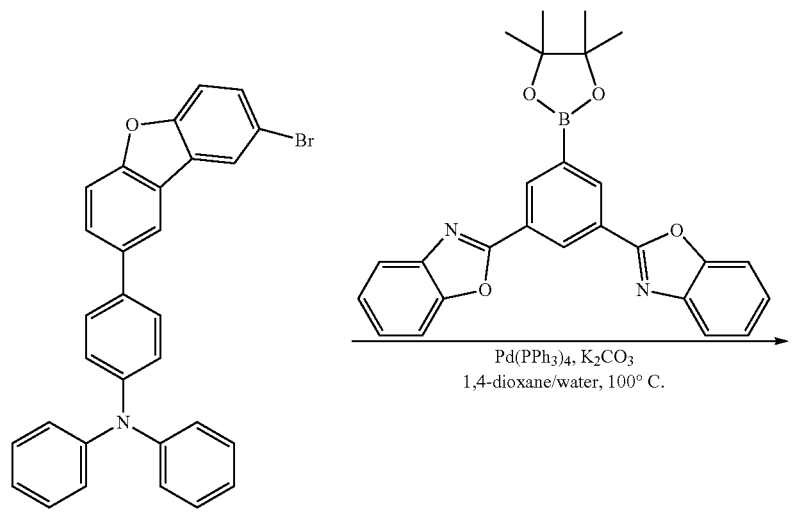
16
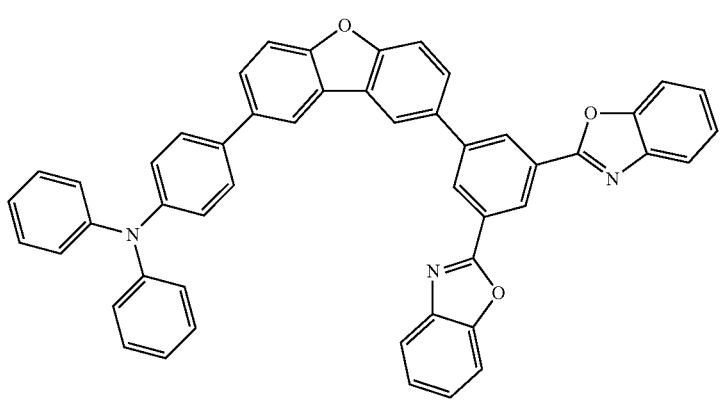
Host-10

Example 1.12.16

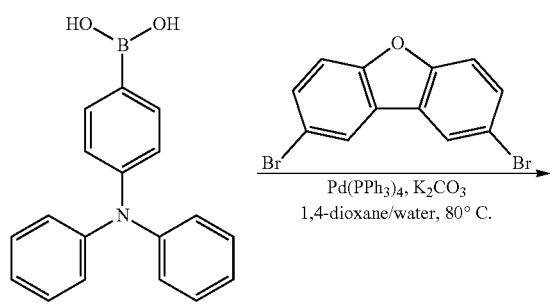

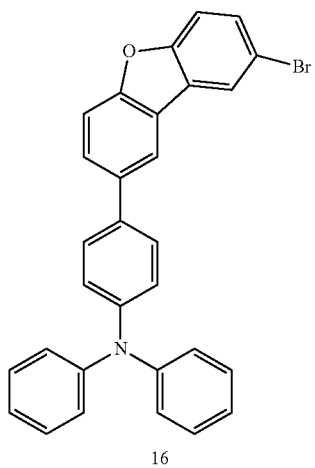

4-(8-(3,5-bis(benzo[d]oxazol-2-yl)phenyl)dibenzo[b,d]furan-2-yl)-N,N-diphenylaniline (Compound 16)

A mixture of (4-(diphenylamino)phenyl)boronic acid (2.00 g, 6.92 mmol), 2,8-dibromodibenzo[b,d]furan (3.95 g, 12.10 mmol), tetrakis(triphenylphosphine) palladium(0) (0.40 g, 0.35 mmol), potassium carbonate (2.87 g, 20.80 mmol), 1,4-dioxane (60.00 mL), and water (12.00 mL) was degassed with bubbling argon for 1 hour. The reaction mixture was then heated to 80° C. and was stirred overnight (16.5 hours), maintaining an argon atmosphere. Consumption of the starting material was confirmed by thin-layer chromatography and the reaction was cooled to room temperature. After adding water, the precipitated product was filtered, dried, and purified by silica gel column chromatography with dichloromethane in hexanes as the eluent. The product fractions were then dried and the product was collected to yield Compound 16 (1.84 g, 54%). Confirmed by LCMS (APCI): calculated for $C_{30}H_{20}BrNO$ (M+H): 490. Found: 490.

Example 1.12

Host-10

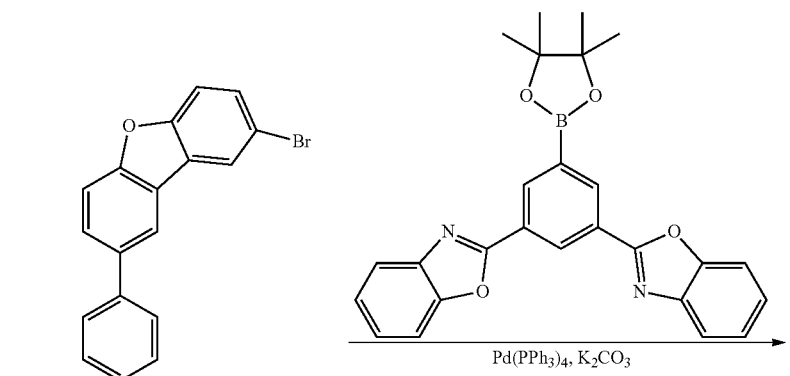

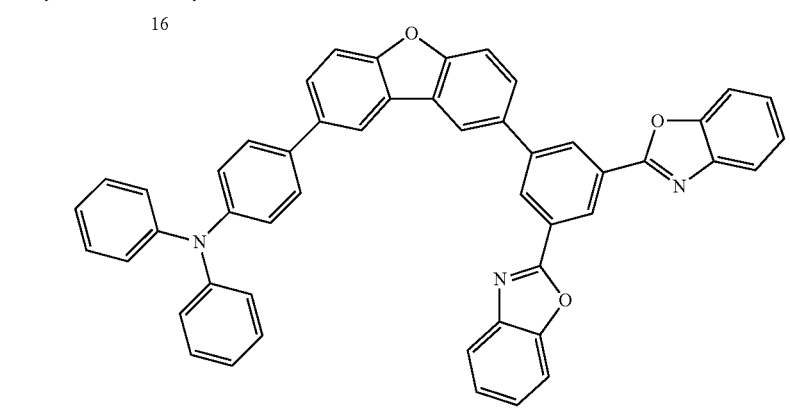

Host-10

Host-10: 4-(8-(3,5-bis(benzo[d]oxazol-2-yl)phenyl)dibenzo[b,d]furan-2-yl)-N,N-diphenylaniline A mixture of Compound 16 (1.00 g, 2.00 mmol), 2,2'-(5-(4,4,5,5-tetramethyl-1,3,2-dioxaborolan-2-yl)-1,3-phenylene)bis(benzo[d]oxazole) (0.98 g, 2.24 mmol), tetrakis(triphenylphosphine) palladium(0) (0.12 g, 0.10 mmol), potassium carbonate (0.85 g, 6.12 mmol), 1,4-dioxane (25.00 mL), and water (5.00 mL) was degassed with bubbling argon for 15 minutes. The reaction was then heated to 100° C. and stirred overnight (16.5 hours), maintaining an argon atmosphere. The precipitated product was filtered, dried, washed with dichloromethane, and recrystallized from chloroform/acetone. The recrystallized product was collected to yield Host-10 (1.08 g, 73%). Confirmed by LCMS (APCI): calculated for $C_{50}H_{31}N_3O_3$ (M+H): 722. Found: 722.

Example 1.13

Synthesis of Host-11

Example 1.13.17

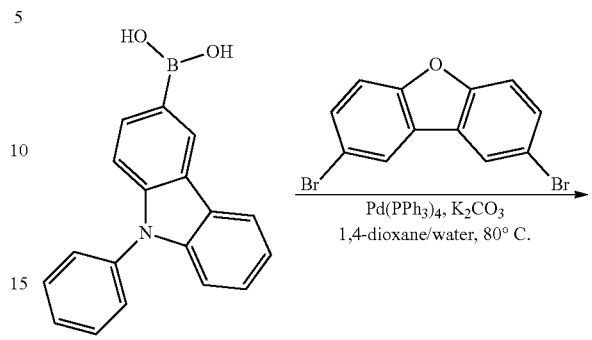

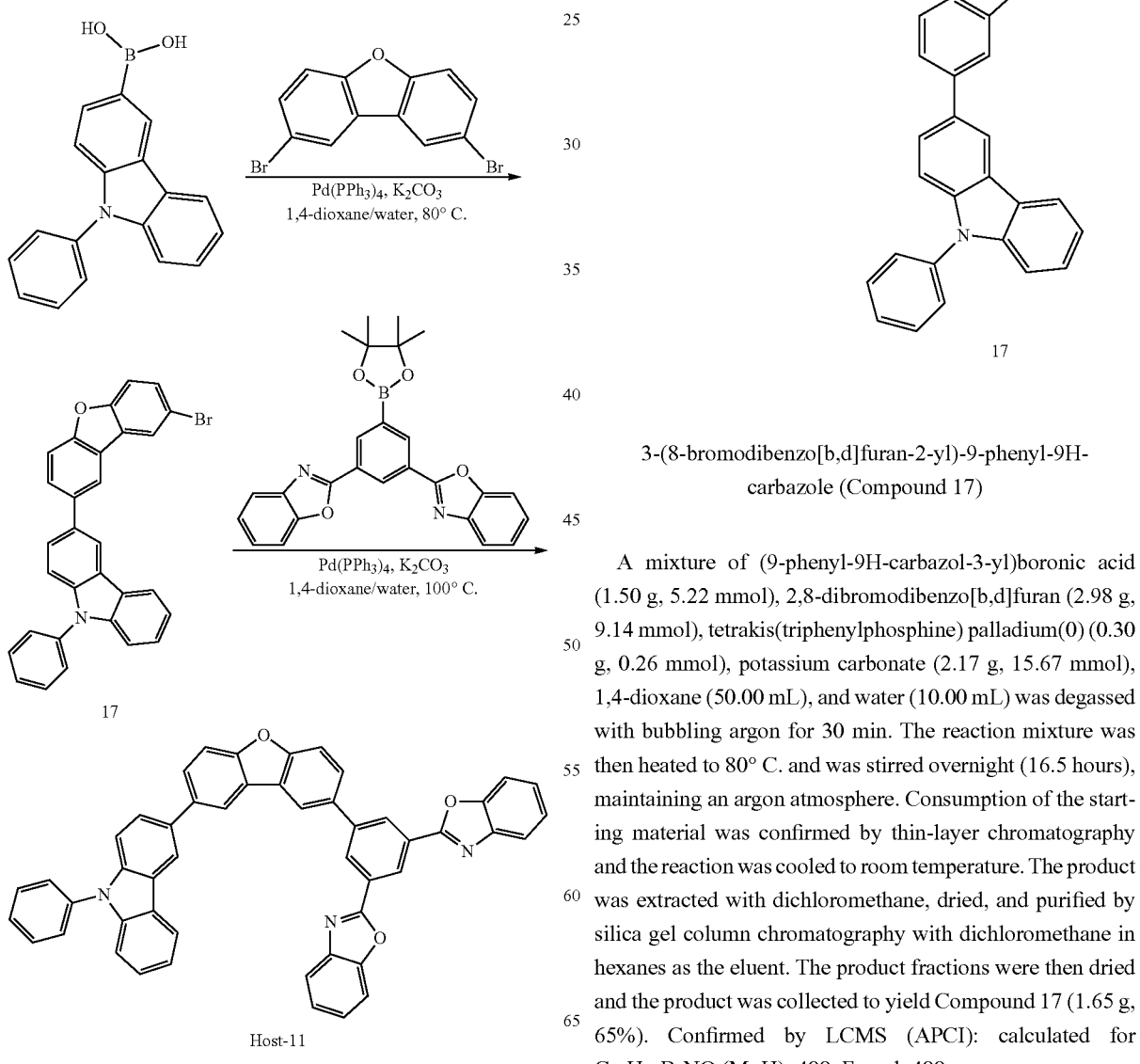

3-(8-bromodibenzo[b,d]furan-2-yl)-9-phenyl-9H-carbazole (Compound 17)

A mixture of (9-phenyl-9H-carbazol-3-yl)boronic acid (1.50 g, 5.22 mmol), 2,8-dibromodibenzo[b,d]furan (2.98 g, 9.14 mmol), tetrakis(triphenylphosphine) palladium(0) (0.30 g, 0.26 mmol), potassium carbonate (2.17 g, 15.67 mmol), 1,4-dioxane (50.00 mL), and water (10.00 mL) was degassed with bubbling argon for 30 min. The reaction mixture was then heated to 80° C. and was stirred overnight (16.5 hours), maintaining an argon atmosphere. Consumption of the starting material was confirmed by thin-layer chromatography and the reaction was cooled to room temperature. The product was extracted with dichloromethane, dried, and purified by silica gel column chromatography with dichloromethane in hexanes as the eluent. The product fractions were then dried and the product was collected to yield Compound 17 (1.65 g, 65%). Confirmed by LCMS (APCI): calculated for $C_{30}H_{18}BrNO$ (M+H): 488. Found: 488.

Example 1.13

Host-11

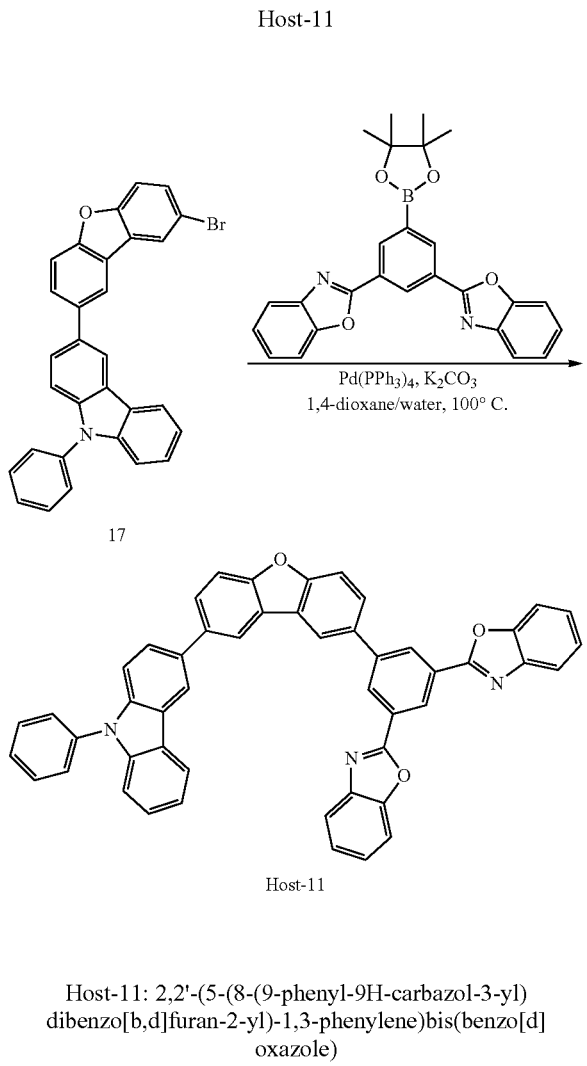

Host-11: 2,2'-(5-(8-(9-phenyl-9H-carbazol-3-yl)dibenzo[b,d]furan-2-yl)-1,3-phenylene)bis(benzo[d]oxazole)

A mixture of Compound 17 (1.25 g, 2.56 mmol), 2,2'-(5-(4,4,5,5-tetramethyl-1,3,2-dioxaborolan-2-yl)-1,3-phenylene)bis(benzo[d]oxazole) (1.23 g, 2.82 mmol), tetrakis(triphenylphosphine) palladium(0) (0.15 g, 0.13 mmol), potassium carbonate (1.06 g, 7.68 mmol), 1,4-dioxane (35.00 mL), and water (7.00 mL) was degassed with bubbling argon for 20 minutes. The reaction was then heated to 100° C. and stirred overnight (16.5 hours), maintaining an argon atmosphere. After adding water, the precipitated product was filtered, dried, washed with dichloromethane, and recrystallized from chloroform/acetone. The recrystallized product was collected to yield Host-11 (1.13 g, 61%). Confirmed by LCMS (APCI): calculated for $C_{50}H_{29}N_3O_3$ (M+H): 720. Found: 720.

Example 2

Experimental SectionsExample 2.1.1

Photoluminescence (PL) spectra was recorded on Fluoro-Max-3 fluorescence spectrophotometer (Horiba Jobin Yvon, Edison, N.J., USA). 2-ethyltetrahydrofuran (2-eTHF) (Aldrich, spectroscopic grade) was used as received. 2 M (2 mg of sample/1 mL of 2-eTHF) was prepared and then transferred to quartz tube prior to measurement. Then, the sample was frozen by liquid nitrogen at 77K. Phosphorescent emission spectrum was recorded and the highest-energy vibronic band was determined to calculate (T1) energy level.

Example 2.1.2

Cyclic voltammetry (CV) was carried out in nitrogen-purged anhydrous N,N-dimethylformamide (DMF) (Aldrich) at room temperature with Echo-Chemie potentiostat/galvonostat (Echo Chemie/Metrohm Autolabe B.V., Utrecht, the Netherlands) Tetra-n-butylammonium hexafluorophosphate ($TBAPF_6$) and DMF were purchased from Aldrich and used as received. Supporting electrolyte solution (0.1 M) with $TBAPF_6$ and analyte, e.g., Host-1, (0.1 mM) in DMF was used for CV study. Formal potentials were calculated as the average of cyclic voltammetric anodic and cathodic peaks and ferrocenium-ferrocene (Fc+/Fc) as the internal standard was introduced to calibrate HOMO (highest occupied molecular orbital) and LUMO (lowest occupied molecular orbital) energy at each experiment. Scan rate of 100 mV/s was used unless otherwise.

Example 2.1.3

Triplet ($T_1$) Energy CalculationTriplet energy was recorded on a Fluoromax-3 spectrometer (Jobin Yvon Horiba, Edison, N.J.) with phosphorescence spectra at 77K. It was determined by the highest-energy vibronic sub-band of the phosphorescence spectra of the desired compound and its wavelength was then converted to triplet energy (eV), as seen in Table-1.

Example 2.1.4

HOMO/LUMO Energy Calculation

HOMO energy was directly determined by oxidation potential of respective compound with respect to redox of ferroceneerrocenium in anodic scan in DMF. Potential difference between the respective compound and ferrocen/ferrocium was determined. Therefore, using vacuum level of ferrocene as the so determined difference, the HOMO of desired compound was determined. The respective LUMO energy was then determined by reduction potential of respective compound with respect to redox of ferrocen/ferrocenium in cathodic scan in DMF. Optical band gap energy of Eg (eV) was estimated by on-set value of UV-vis spectroscopy, 3.04 eV and 2.99 eV, respectively, were measured for Host-1-Host-11 and then LUMO was calculated as set forth in Table-1.

TABLE-1

|        | HOMO  | LUMO  | T1   | λem | Tg  |
|--------|-------|-------|------|-----|-----|
| Host-1 | −5.71 | −2.27 | 2.54 | 397 | 148 |
| Host-2 | −5.71 | −2.34 | 2.45 | 407 | 156 |
| Host-3 | −5.8  | −2.28 | 2.70 | 398 | 171 |

TABLE-1-continued
| | | HOMO | LUMO | T1 | λem | Tg |
|---|---|---|---|---|---|---|
| Host-4 | 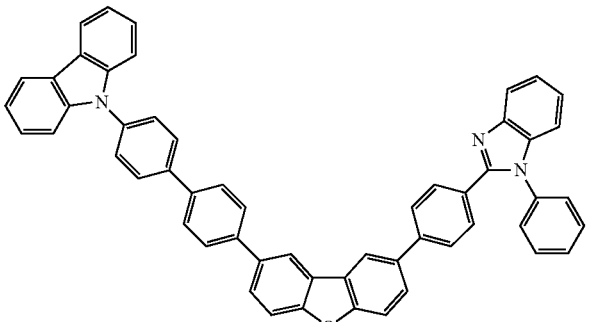 | −5.67 | −2.17 | 2.53 | 393 | 162 |
| Host-5 | 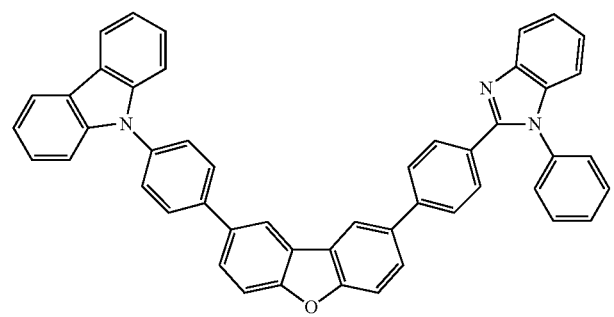 [SMILES: c1ccc(-n2c(-c3ccc(-c4ccc5oc6ccc(-c7ccc(-n8c9ccccc9c9ccccc98)cc7)cc6c5c4)cc3)nc3ccccc32)cc1] | −5.69 | −2.22 | 2.54 | 394 | 151 |
| Host-6 | 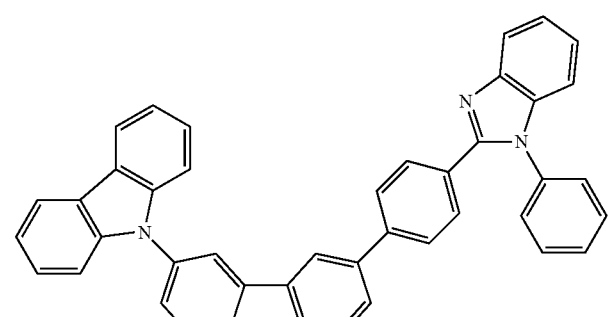 | −5.71 | −2.19 | 2.54 | 401 | 141 |
| Host-7 | 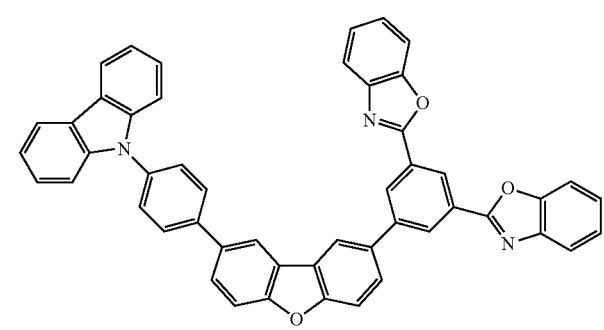 [SMILES: c1ccc2oc(-c3cc(-c4ccc5oc6ccc(-c7ccc(-n8c9ccccc9c9ccccc98)cc7)cc6c5c4)cc(-c4nc5ccccc5o4)c3)nc2c1] | n/a | n/a | 2.63 | 409 | n/a |

TABLE-1-continued
| | HOMO | LUMO | T1 | λem | Tg |
|---|---|---|---|---|---|
| Host-8 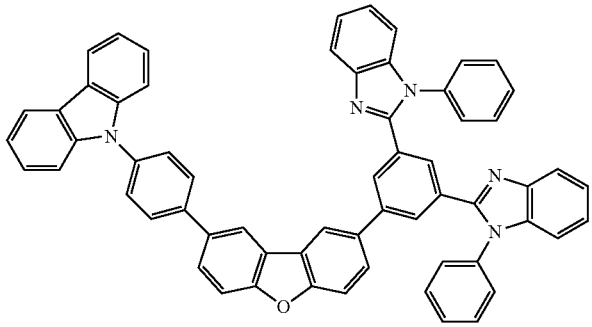 [SMILES: c1ccc(-n2c(-c3cc(-c4ccc5oc6ccc(-c7ccc(-n8c9ccccc9c9ccccc98)cc7)cc6c5c4)cc(-c4nc5ccccc5n4-c4ccccc4)c3)nc3ccccc32)cc1] | −5.69 | −2.22 | 2.7 | 383 | 172 |
| Host-9 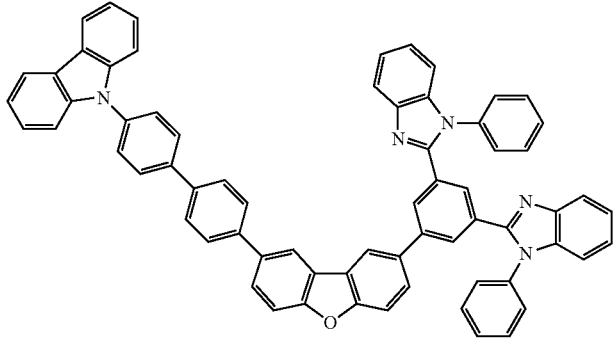 [SMILES: c1ccc(-n2c(-c3cc(-c4ccc5oc6ccc(-c7ccc(-c8ccc(-n9c%10ccccc%10c%10ccccc%109)cc8)cc7)cc6c5c4)cc(-c4nc5ccccc5n4-c4ccccc4)c3)nc3ccccc32)cc1] | −5.68 | −2.22 | 2.51 | 399 | 176 |
| Host-10 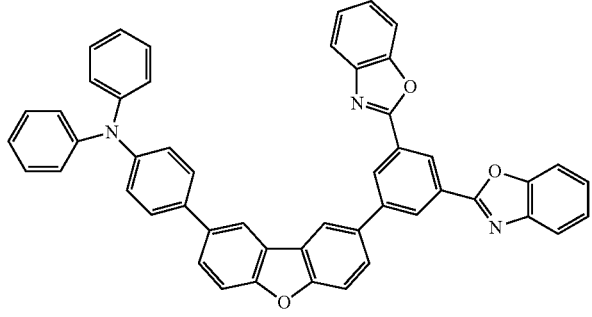 [SMILES: c1ccc(N(c2ccccc2)c2ccc(-c3ccc4oc5ccc(-c6cc(-c7nc8ccccc8o7)cc(-c7nc8ccccc8o7)c6)cc5c4c3)cc2)cc1] | −5.35 | −2.54 | 2.59 | 454 | n/a |
| Host-11 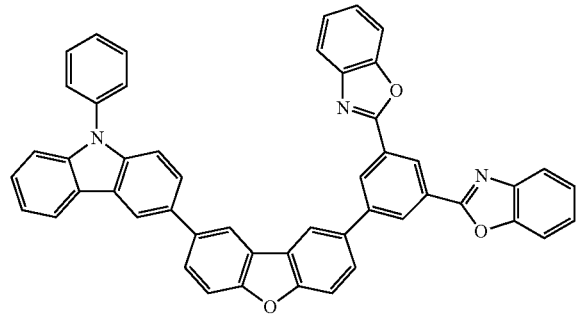 [SMILES: c1ccc(-n2c3ccccc3c3cc(-c4ccc5oc6ccc(-c7cc(-c8nc9ccccc9o8)cc(-c8nc9ccccc9o8)c7)cc6c5c4)ccc32)cc1] | −5.62 | −2.6 | 2.63 | 451 | n/a |

Example 3

OLED Device Configuration and PerformanceExample 3.1

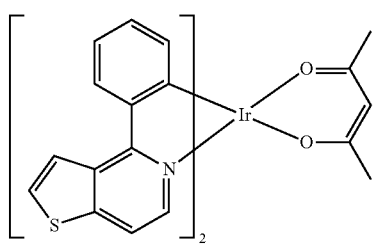

YE-1

A device will be fabricated in a manner similar to the following. The ITO substrates having sheet resistance of about 14 ohm/sq will be cleaned ultrasonically and sequentially in detergent, water, acetone and then IPA; and then dried in an oven at about 80° C. for about 30 min under ambient environment. Substrates will be baked at about 200° C. for about 1 hour in an ambient environment, then under UV-ozone treatment for about 30 minutes. PEDOT:PSS (hole-injection material) will then be spin-coated on the annealed substrate at about 5000 rpm for about 30 sec. The coated layer will then be baked at about 100° C. for 30 min in an ambient environment, followed by baking at about 200° C. for 30 min inside a glove box ($N_2$ environment). The substrate will then be transferred into a vacuum chamber, where 4,4',4"-tri(N-carbazolyl)triphenylamine (TCTA [hole transporting material]) will be vacuum deposited at a rate of about 0.1 nm/s rate under a base pressure of about $2 \times 10^{-7}$ torr. An electroluminescent compound, e.g., YE-1 (10 wt %) will be co-deposited as an emissive layer with one of either Host-1-Host-11 material at about 0.01 nm/s and about 0.10 nm/s, respectively, to make the appropriate thickness ratio. 1,3,5-Tris(1-phenyl-1H-benzimidazol-)2-yl)benzene (TPBI) will then be deposited at about 0.1 nm.s rate on the emissive layer. A layer of lithium fluoride (LiF) (electron injection material) will be deposited at about 0.005 nm/s rate followed by deposition of the cathode as Aluminum (Al) at about 0.3 nm/s rate.

The representative device structure will be, although is not limited by: ITO (about 150 nm thick)/PEDOT:PSS (about 40 nm thick)/TCTA (about 40 nm thick)/any of Host-1-Host-11 coupled with an electroluminescent compound (about 30 nm thick)/TPBI (about 30 nm thick)/LiF (about 0.5 nm thick)/Al (about 100 nm thick). The device will then be encapsulated with a glass cap to cover the emissive area of the OLED device in order to protect from moisture, oxidation or mechanical damage.

While the invention has been described in detail, the foregoing description is in all aspects illustrative and not restrictive. Thus, in view of the present disclosure which describes the current best mode for the creation and implementation of the chemical compounds, it will be clear to those of skill in the art that many modifications and variations present themselves without creating a divide from the scope and spirit of the invention. The scope of the invention is, therefore, indicated by the following claims rather than by the foregoing descriptions and drawings. Accordingly, all changes, modifications, and variations are not to be restricted except in light of the attached claims and their equivalents.

What is claimed is:

1. A compound represented by the formula:

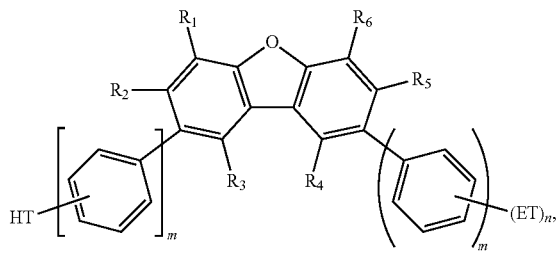

where $R_1$, $R_2$, $R_3$, $R_4$, $R_5$ and $R_6$ are independently H, $C_1$-$C_3$ alkyl, or $C_{1-3}$ perfluoroalkyl; HT is optionally substituted carbazoyl, optionally substituted phenyl-naphthylamine, or optionally substituted diphenylamine, where each m is independently 0, 1, or 2; and ET is selected from optionally substituted benzimidazol-2-yl, optionally substituted benzothiazol-2-yl, optionally substituted benzoxazol-2-yl, optionally substituted 3,3'-bipyridin-5-yl, optionally substituted quinolin-8-yl, optionally substituted quinolin-5-yl, and optionally substituted quinoxalin-5-yl, where n is 1 or 2.

2. The compound of claim 1 wherein $R_1$, $R_2$, $R_3$, $R_4$, $R_5$ and $R_6$ are H.

3. The compound of claim 1 wherein HT is selected from:

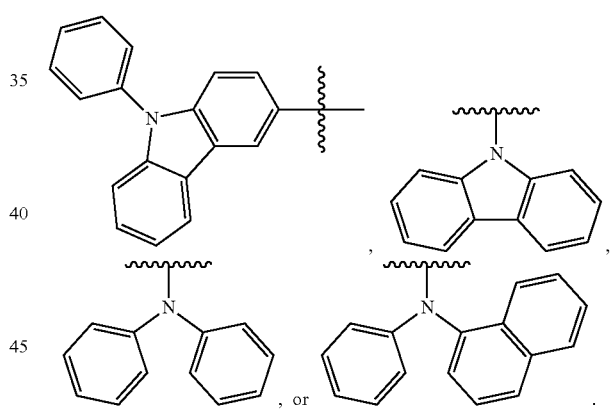

4. The compound of claim 1 wherein ET is selected from:

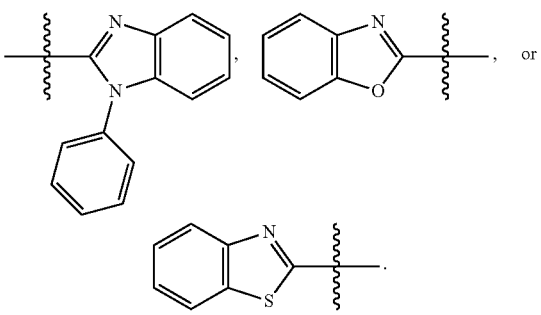

5. The compound of claim 1 wherein the compound is selected from:

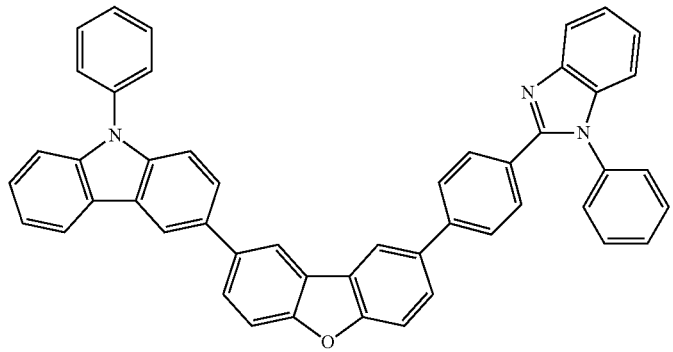
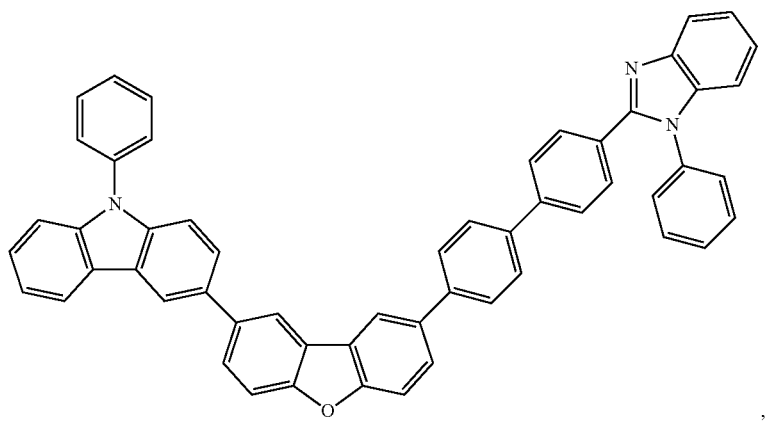
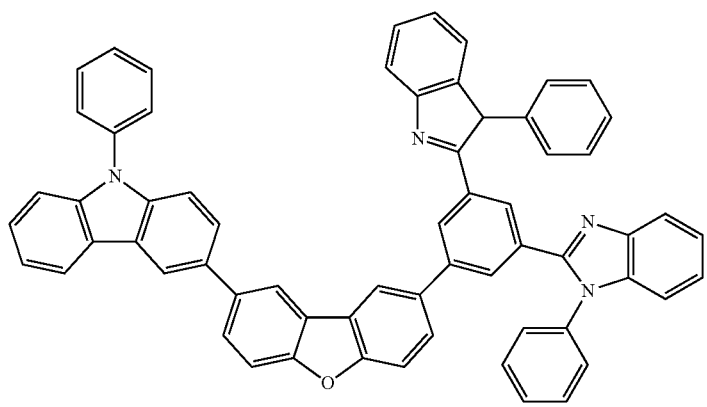
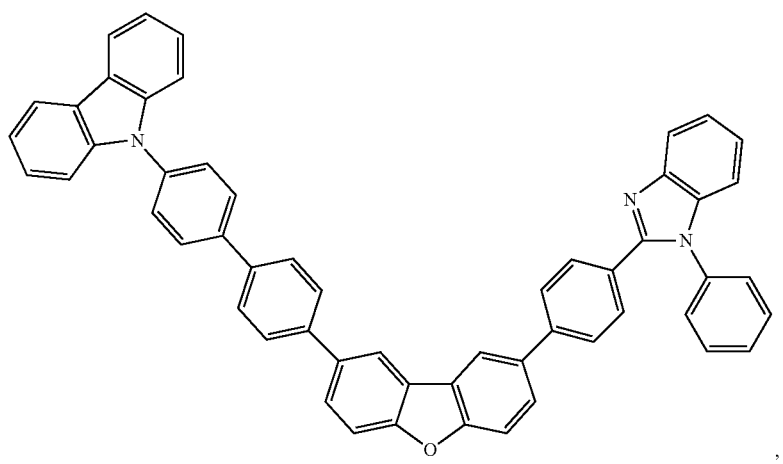

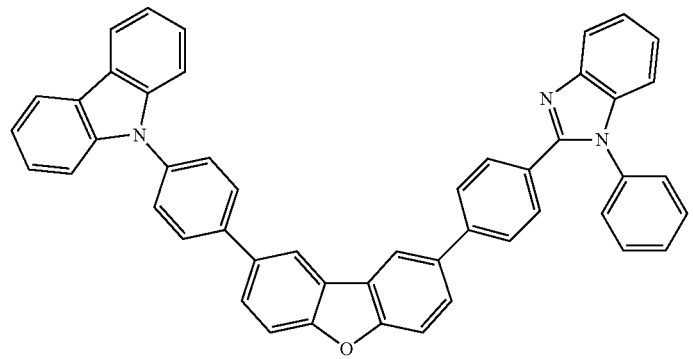,
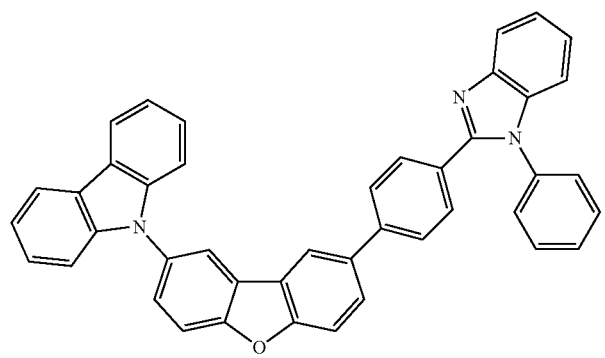,
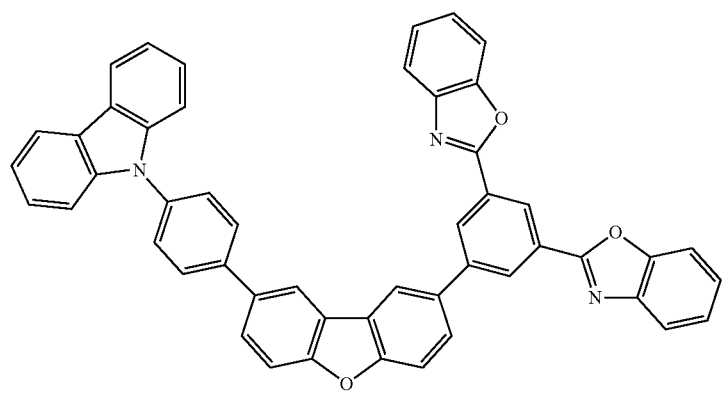,
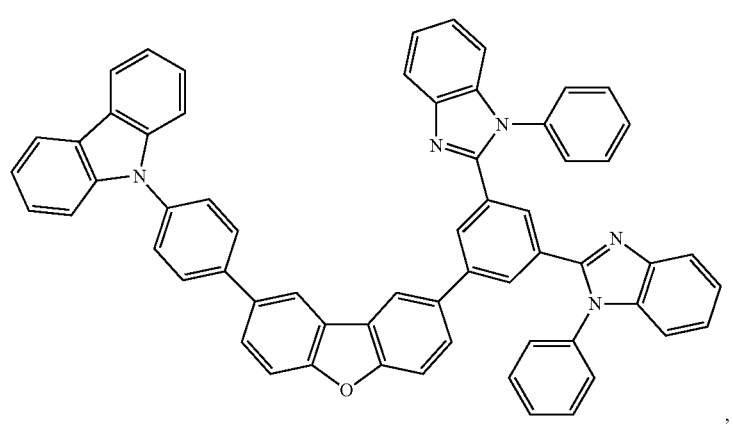,

-continued

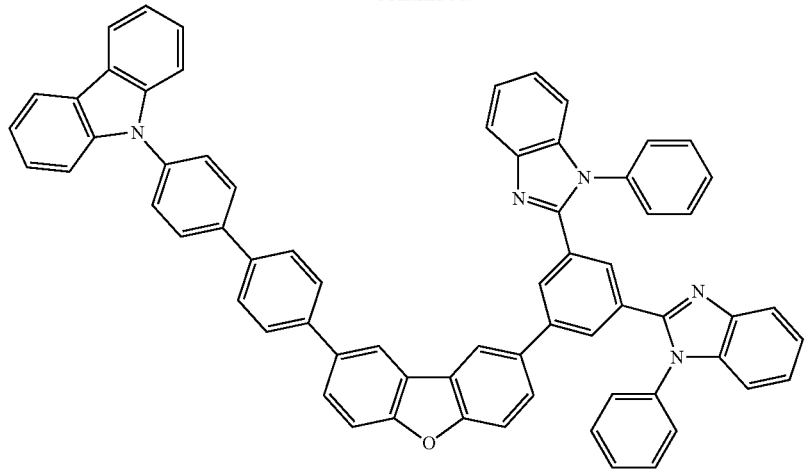

,

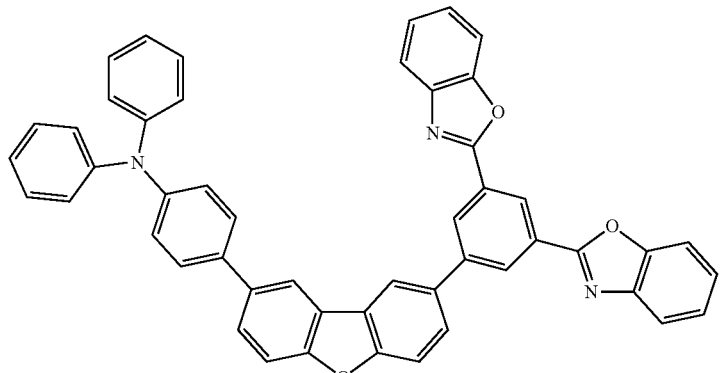

, or

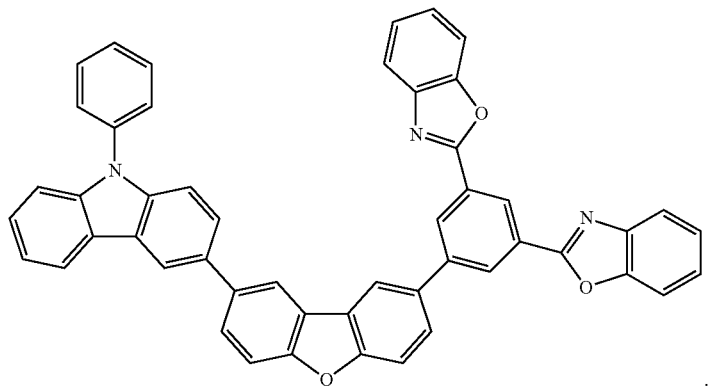 [SMILES: c1ccc(-n2c3ccccc3c3cc(-c4ccc5oc6ccc(-c7cc(-c8nc9ccccc9o8)cc(-c8nc9ccccc9o8)c7)cc6c5c4)ccc32)cc1]

.

6. An OLED device comprising a compound of claim 1.

7. The OLED device of claim 6 wherein said compound is a host compound in a light-emitting layer.

8. The OLED device of claim 7 further comprising a hole-transport layer disposed between the light-emitting layer and an anode.

9. The OLED device of claim 7 further comprising an electron-transport layer disposed between the light-emitting layer and a cathode.

10. The OLED device of claim 8 further comprising an electron-transport layer disposed between the light-emitting layer and a cathode.

* * * * *